United States Patent [19]

Mallams et al.

[11] Patent Number: 4,962,146
[45] Date of Patent: Oct. 9, 1990

[54] 3-O-GLYCOSYL 16-MEMBERED MACROLIDE ANTIBACTERIALS AND RELATED DERIVATIVES

[75] Inventors: Alan K. Mallams, West Orange; Randall R. Rossman, Nutley; Olga Sarre, Verona; Viyyoor M. Girijavallabhan, Parsippany; Ashit K. Ganguly, Upper Monclair, all of N.J.

[73] Assignee: Schering Corporation, Kenilworth, N.J.

[21] Appl. No.: 259,455

[22] Filed: Oct. 14, 1988

Related U.S. Application Data

[63] Continuation of Ser. No. 44,076, Apr. 29, 1987, abandoned.

[51] Int. Cl.$^5$ .................. A61K 31/70; C07H 17/08
[52] U.S. Cl. ............................ 514/30; 536/7.1
[58] Field of Search .................. 536/7.1; 514/30

[56] References Cited

U.S. PATENT DOCUMENTS

| | | | |
|---|---|---|---|
| 3,178,341 | 4/1965 | Hamill et al. | 536/7.1 |
| 3,326,759 | 6/1967 | Hamill et al. | 424/120 |
| 3,769,273 | 10/1973 | Massey | 536/7.1 |
| 3,975,372 | 8/1976 | Ganguly et al. | 536/7.1 |
| 4,056,616 | 11/1977 | Reimann et al. | 536/7.1 |
| 4,161,523 | 7/1979 | Weinstein et al. | 536/7.1 |
| 4,234,690 | 11/1980 | Weinstein et al. | 439/119 |
| 4,252,898 | 2/1981 | Nash et al. | 536/7.1 |
| 4,321,361 | 3/1982 | Baltz et al. | 536/7.1 |
| 4,345,069 | 8/1982 | Sakakibara et al. | 536/7.1 |
| 4,357,325 | 11/1982 | Ose et al. | 536/7.1 |
| 4,415,730 | 11/1983 | Fujiwara et al. | 536/7.1 |
| 4,454,314 | 6/1984 | Nagel | 536/7.1 |
| 4,477,443 | 10/1984 | Umezawa et al. | 536/7.1 |
| 4,528,369 | 7/1985 | Wild | 536/7.1 |

FOREIGN PATENT DOCUMENTS 57-05000  1/1982  Japan .................. 536/7.1

OTHER PUBLICATIONS

Chemical Abstracts, vol. 102, (No. 15), Apr. 15, 1985, Abstract No. 132421x.
Chemical Abstracts, vol. 108, (No. 19), Sep. 9, 1987, Abstract No. 167885c.
Djerassi et al., J. Am. Chem. Soc., 1956, vol. 78, pp. 6390–6395.
Wiley et al., J. Am. Chem. Soc., 1957, vol. 79, pp. 6062–6072.
Djerassi et al., Tetrahedron, 1958, vol. 3, pp. 255–268.
Straustz et al., J. Am. Chem. Soc., 1960, vol. 82, pp. 3225–3227.
Egan et al., J. Am. Chem. Soc., 1970, vol. 92, pp. 4129–4130.
Pigman et al., *The Carbohydrates*, Academic Press., 2nd Ed., 1980, pp. 767–798.
Brimacombe et al., J. Chem. Soc., Perkin Trans. I, 1982, pp. 2583–2587.

*Primary Examiner*—Johnnie R. Brown
*Assistant Examiner*—Elli Peselev
*Attorney, Agent, or Firm*—Thomas D. Hoffman; Gerald S. Rosen

[57] ABSTRACT

3-O-Glycosyl derivatives of 16-membered macrolides such as O-α-L-cladinosyl-(1→3)-12,13-dehydro-12,13-deoxorosaramicin, 2″,4″,4‴-tri-O-acetyl-O-(4′-O-phenoxyacetyl-α-L-cladinosyl)-(1→3)-desmycosin and pharmaceutically acceptable acid addition salts thereof useful as antibacterials are disclosed.

34 Claims, No Drawings

3-O-GLYCOSYL 16-MEMBERED MACROLIDE ANTIBACTERIALS AND RELATED DERIVATIVES

This is a continuation of application Ser. No. 044,076 filed 4/29/87, now abandoned.

BACKGROUND OF THE INVENTION

This invention relates to 3-O-glycosyl 16-membered macrolide antibacterials, such as 2'',4'',4'''-tri-O-acetyl-O-(4'-O-phenoxyacetyl-α-L-cladinosyl)-(1→3)-desmycosin and O-α-L-cladinosyl-(1→3)-12,13-dehydro-12,13-deoxorosaramicin, related derivatives, pharmaceutically acceptable acid addition salts thereof, and pharmaceutical compositions containing them and a method of eliciting an antibacterial response using the 3-O-glycosyl 16-membered macrolide antibacterials or pharmaceutical compositions containing them.

Several 3-O-glycosyl derivatives are found among the naturally occurring 12- and 14-membered macrolides. For example, among the 12-membered macrolides, methymycin is disclosed in *J. Am. Chem. Soc.*, 1956, 78, p. 6390, and neomethymycin is disclosed in *Tetrahedron*, 1958, 3, p. 255. Among the 14-membered macrolides, erythromycin is disclosed in *J. Am. Chem. Soc.*, 1957, 79, p. 6062; oleandomycin is disclosed in *J. Am. Chem. Soc.*, 1960, 82, p. 3225; and lankamycin is disclosed in *J. Am. Chem. Soc.*, 1970, 92, P. 4129. There is no disclosure of 3-O-glycosyl 16-membered macrolide antibacterials available synthetically or occuring naturally.

SUMMARY OF THE INVENTION

In accordance with this invention, there is provided a compound represented by formula I:

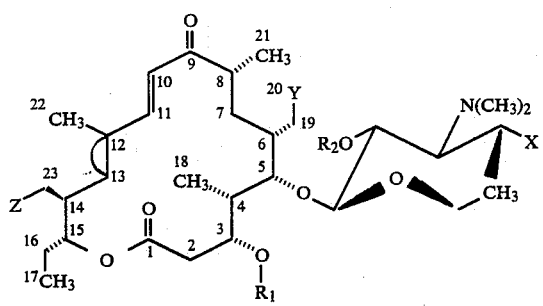

I wherein $R_1$ is a glycosyl group, represented by the formula II:

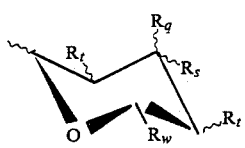

II wherein $R_q$ and $R_t$ independently hydrogen, hydroxy, acyloxy, loweralkoxy, aralkoxy, N-loweralkylaminocarbonyloxy, N-aralkylamino carbonyloxy, or arylsulfonyloxy ($-OSO_2Ar$) and $R_s$ and $R_w$ are independently hydrogen, lower alkyl or $-CH_2OH$; or represented by the formula IIA:

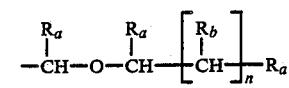

IIA wherein $R_a$ is hydrogen, lower alkyl, or $CH_2OH$ and $R_b$ is hydrogen, hydroxy, acyloxy, lower alkoxy, aralkoxy, N-loweralkylaminocarbonyloxy, N-aralkylaminocarbonyloxy or arylsulfonyloxy and n is 1, 2, 3, or 4;

$R_2$ is hydrogen or an acyl group;
X is hydrogen, hydroxy, an acyloxy group

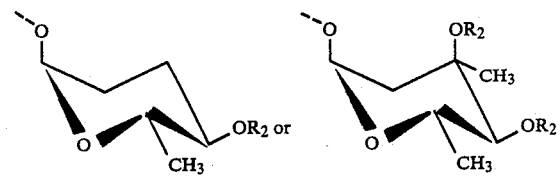

wherein $R_2$ is defined as hereinabove;
Y is hydrogen, a formyl group, methyl,

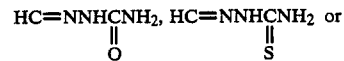

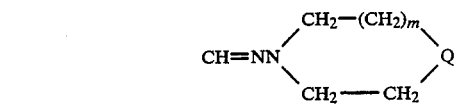

wherein m is 0,1, or 2 and Q is independently $CR_3R_4$, $NR_3$, O, S, $SO_2$, $CR_3OR_4$,

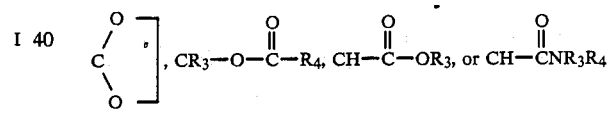

wherein $R_3$ and $R_4$ are independently hydrogen, lower alkyl, aralkyl, G-substituted aralkyl, aryl and G-substituted aryl wherein G is independently one or more of halogen, trifluoromethyl, lower alkoxy or ($C_2-C_7$)alkanoyl;
 is a 12,13 double bond or a 12,13-oxo moiety; Z is hydrogen, hydroxy, an acyloxy group, a N,N-di(lowralkyl)amino group or

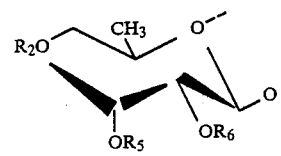

loweralkoxycarbonyloxy, aralkoxycarbonyloxy, N-loweralkylaminocarbonyloxy, and N-aralkylaminocarbonyloxy wherein $R_2$ is defined above and $R_5$ and $R_6$ are independently hydrogen, lower alkyl or acyl groups; or a pharmaceutically acceptable acid addition salt thereof.

The compounds of this invention show high serum levels and are useful as antibacterials against susceptible bacterial infections, especially those caused by Gram-positive organisms.

This invention also provides a pharmaceutical composition comprising an antibacterially effective amount of a compound represented by formula I in admixture with a pharmaceutically acceptable carrier therefor.

This invention further provides a method of eliciting an antibacterial effect against susceptible bacterial infections, wherein an antibacterially effective amount of a compound represented by formula I or nharmaceutical compositions thereof is administered to an animal having a susceptible bacterial infection.

The compounds of this invention have stereochemical configuration indicated for the structure of compounds of formula I, and it is to be understood that the stereochemical configuration is identical to that of tylosin. The stereochemistry of the 12,13-oxo moiety, when present in the compounds of formula I, is indicated below:

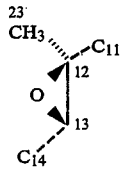

and it is to be understood that the stereochemical configuration is identical to the stereochemistry of the 12,13-oxo-16-membered macrolides disclosed in co-pending commonly assigned U.S. patent application Ser. No. 877,079, filed June 23, 1986.

DETAILED DESCRIPTION OF THE INVENTION

The term "acyl group" as used herein means ($C_2$-$C_7$)alkanoyl, ($C_2$-$C_7$)alkanoyl substituted lower alkoxy, aryl or aryloxy, aroyl and substituted aroyl or substituted aryloxy said aroyl and aryloxy substituents being one or more of halogen, nitro, lower alkoxy, or lower alkyl.

The term "acyloxy" means the "acyl group" as defined herein univalently bonded to divalent oxygen and includes inter alia, acetyloxy, butyryloxy, iso-valeryloxy, phenylacetyloxy, benzoyloxy, p-methoxybenzoyloxy.

The term "lower alkyl" as used herein means straight and branched-chain alkyl groups of one to six carbons including methyl, ethyl, propyl, butyl, pentyl, hexyl and the corresponding branched-chain isomers thereof such as iso-propyl, tert- or sec-butyl, iso-valeryl and iso-hexyl. Methyl is the preferred alkyl group.

The term "lower alkoxy" means "lower alkyl" groups univalently bonded to divalent oxide and includes inter alia, methoxy, ethoxy, and propoxy.

The term "aryl" means phenyl and biphenyl.

The term "halogen" means fluoro, chloro and bromo, preferably fluoro and chloro.

The term "aralkyl" means aralkyl means lower alkyl substituted by aryl including benzyl, α-and -βphenethyl and α- and β-(o-tolyl)ethyl.

"Aralkoxy" refers to "aralkyl" as defined hereinabove univalently bonded to divalent oxygen.

The term "aryloxy" refers to phenoxy, benzyloxy and biphenyloxy.

The term "($C_2$-$C_7$)alkanoyl" means carbonyl groups univalently bonded to "lower alkyl" groups and includes acetyl, propionyl, butyryl, iso-butyryl and iso-valeryl. The preferred ($C_2$-$C_7$) alkanoyl groups are acetyl, butyryl, iso-valeryl for $R_1$, $R_2$, $R_3$, $R_4$, $R_5$, and $R_6$.

Typical suitable chloro-substituted ($C_2$-$C_7$) alkanoyl groups include 2-chloro($C_2$-$C_7$)alkanoyl such as 2-chloroacetyl and 2-chloropropanoyl. Typical suitable lower alkoxy ($C_2$-$C_7$) alkanoyls include methoxyacetyl, ethoxyacetyl, 2- and 3-methoxypropanoyl, and propoxyacetyl. Typical suitable aryl-substituted ($C_2$-$C_7$) alkanoyl groups include phenylacetyl and biphenylacetyl. Typical suitable aryloxy-substituted ($C_2$-$C_7$)alkanoyls include phenoxyacetyl and biphenyloxyacetyl.

The term "aroyl" means substituted and unsubstituted benzoyl wherein the substituents are one or more of halogen, nitro, lower alkoxy or lower alkyl. Typical suitable substituted benzoyl include p-fluorobenzoyl, 3-chlorobenzoyl, 4-nitrobenzoyl, 3-nitrobenzoyl, p-ethoxybenzoyl, 3-chloro-4-nitrobenzoyl, 3-fluoro-4-methoxybenzoyl, 3-nitro-4-ethylbenzoyl and 3-chloro-4methylbenzoyl.

Typical suitable G-substituted aryl groups include 4-fluorophenyl, 3-chlorophenyl, 4-trifluoromethylphenyl, 4-ethoxyphenyl, 4-acetylphenyl and 3-chloro-4-methoxyphenyl.

Typical suitable G-substituted aralkyl groups include 4-fluorobenzyl, 3-chlorophenylethyl, 4-methoxy-α-phenethyl, and 4-trifluoromethylbenzyl.

The term "N,N-di(loweralkyl)amino" means two "lower alkyl groups", each univalently bonded to a trivalent nitrogen atom, including dimethylamino, diethylamino, di-n-propylamino, methylpropylamino and diisopropylamino.

The term "lower alkoxycarbonyloxy" as used herein means "lower alkoxy" groups univalently bonded to the carbonyl carbon of the carbonyloxy moiety

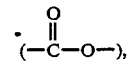

including inter alia, methoxycarbonyloxy, ethoxycarbonyloxy and n- and iso-propoxycarbonyloxy.

The term "aralkoxycarbonyloxy" as used herein means an "aralkyl croup" univalently bonded to a divalent oxide which in turn is univalently bonded to the carbonyl carbon of the carbonyloxy moiety including phenethoxycarbonyloxy, benzyloxycarbonyloxy, and o-tolylethoxycarbonyloxy.

The term "N-loweralkylaminocarbonyloxy" as used herein means one or two "lower alkyl group" univalently bonded to the trivalent amino moiety, —N— which in turn is univalently bonded to the carbonyl carbon of a carbonyloxy moiety, including N-methylaminocarbonyloxy N,N-dimethylaminocarbonyloxy, N-iso-oropylaminocarbonyloxy N,N-methyiethylaminocarbonyloxy and N-tert-butylaminocarbonyloxy. tert-butylaminocarbonyloxy.

The term "N-aralkylaminocarbonyloxy" as used herein means one or two "aralkyl group" univalently bonded to a trivalent nitrogen, i.e. —N— which in turn is univalently bonded to the carbonyl carbon of the carbonyloxy moiety, including N-benzylaminocarbonyloxy, N-(β-phenethyl)aminocarbonyloxy and N-o-tolylethyl-aminocarbonyloxy.

The term "arylsulfonyloxy" means "aryl" univalently bonded to the sulfur in sulfonyloxy including phenylsulfonyloxy and biphenyl sulfonyloxy.

The term "glycosyl group" as used herein means an α- or β-D- or -L-pentopyranosyl group or α- or β-D- or -L-hexopyranosyl group represented by the formula II:

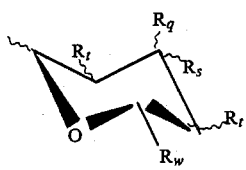

wherein $R_g$ and $R_t$ are independently hydrogen, acyloxy, loweralkoxy, aralkoxy, N-loweralkylaminocarbonyloxy, N-aralkylamino carbonyloxy, or arylsulfonyloxy ($-OSO_2Ar$) and $R_s$ and $R_w$ are independently hydrogen, lower alkyl or $-CH_2OH$ or an acyclic group represented by the formula IIA:

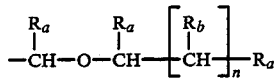
IIA wherein $R_a$ is hydrogen, lower alkyl, or $CH_2OH$ and $R_b$ is hydrogen, hydroxy, acyloxy, loweralkoxy, aralkoxy, N-loweralkylaminocarbonyloxy, N-aralkylaminocarbonyloxy or arylsulfonyloxy and n is 1, 2, 3 or 4.

$R_a$ is preferably hydrogen or methyl. $R_b$ is preferably hydrogen or loweralkoxy.

Typical suitable acyclic glycosyl groups represented by formula IIA include $-CH_2-O-CH_2CH_3$, $-CH(CH_3)-O-CH(CH_3)_2$, $-CH_2-O-(CH_2)_2CH_3$, $-CH_2-O-(CH_2)_3-CH_3$, $-CH(CH_3)-O-CH_2CH(CH_3)_2$, $-CH_2-O-(CH_2)_4-CH_3$, $-CH(CH_3)-O-CH(CH_3)-(CH_2)_3-CH_3$, $-CH_2-O-CH_2CH(OCH_3)CH_3-CH_2-O-CH(CH_2OH)-CH_3$ or $-CH(CH_3)-O-CH(CH_2OH)(CH_2)_3CH_3$.

$R_q$ which may be in the axial (a) position (formula IIB) or equatorial (e) position (formula IID) is preferably hydroxy, methoxy or acyloxy. $R_t$ is preferably hydrogen, hydroxy, lower alkoxy, for example methoxy, or acyloxy, for example acetyloxy, butyryloxy or isovaleryloxy. $R_s$ and $R_w$ may be in the axial or equatorial position. $R_s$ is preferably hydrogen or methyl; $R_w$ is preferably methyl.

The preferred glycosyl groups include the following α-L-glycosyl groups represented by formulas IIB, IIC and IID

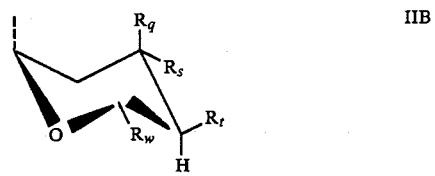
IIB

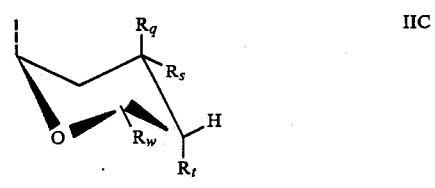
IIC

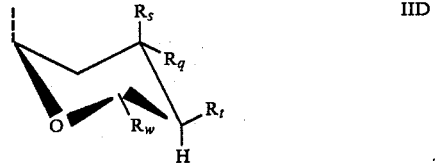
IID wherein $R_s$ and $R_w$ are independently hydrogen and methyl and wherein $R_g$ is hydroxy, lower alkoxy or lower acyloxy and $R_t$ is hydrogen, hydroxy, lower alkoxy or acyloxy:

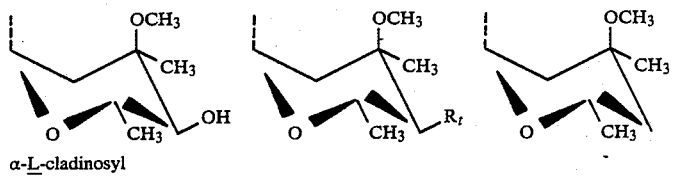

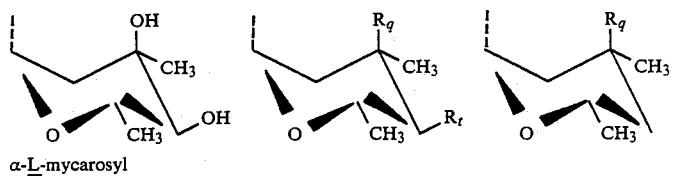

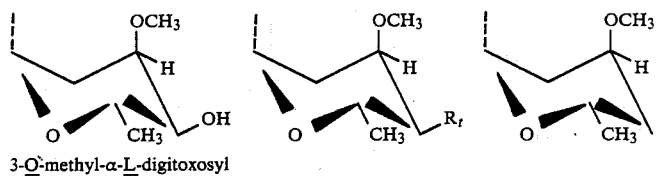

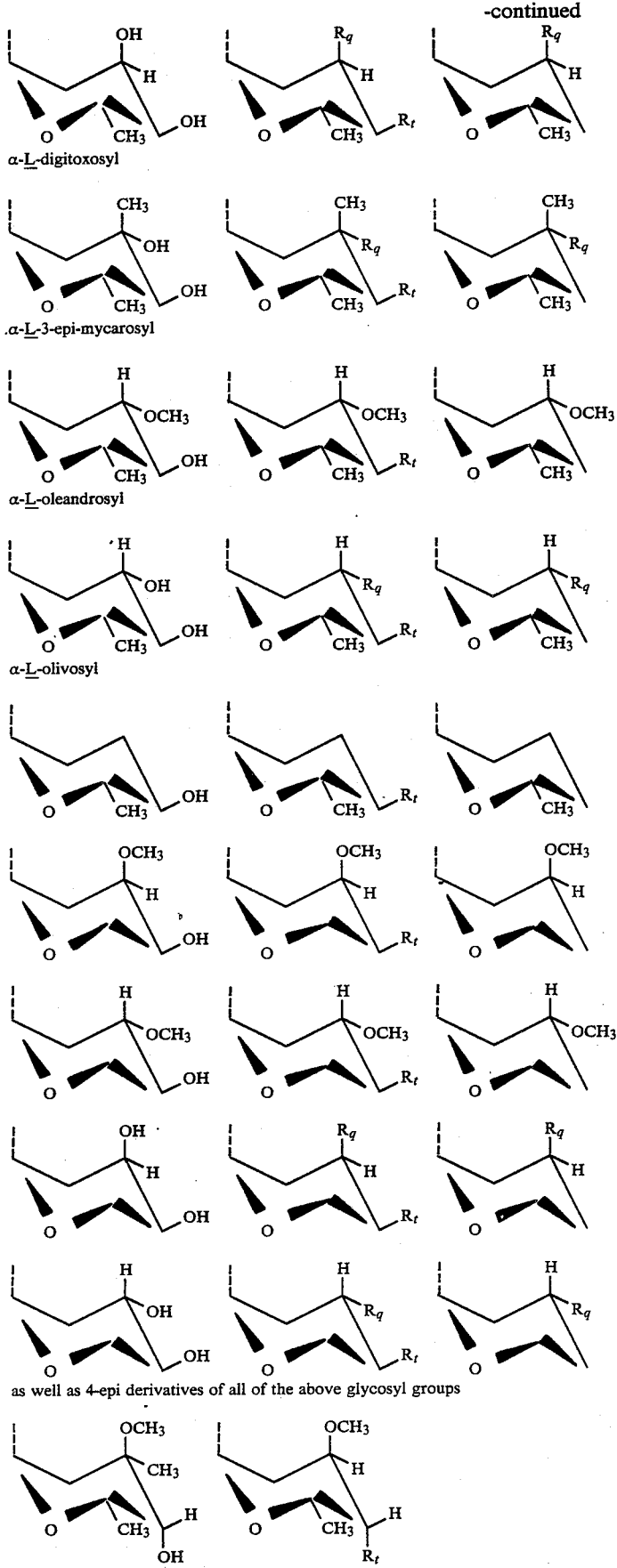
α-L-digitoxosyl
α-L-3-epi-mycarosyl
α-L-oleandrosyl
α-L-olivosyl
as well as 4-epi derivatives of all of the above glycosyl groups α-L-arcanosyl

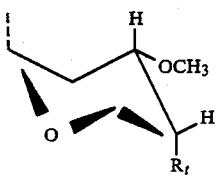

The corresponding β-L-glycoside groups and α- or β-3-tetrahydropyranyl group, i.e.,

The more preferred α-L-glycosyl groups of formula IIB, IIC, and IID are α-L-cladinosyl, 4-O-acyl-α-L-cladinosyl, α-L-digitoxsyl, 3-O-methyl-α-L-digitoxyl, 3,4-di-O-acyl-α-L-digitoxsyl, 3,4-di-O-acyl-α-L-mycarosyl, 4-O-acyl-α-L-oleandrosyl, and 3-tetrahydropyranyl.

The α-L-cladinosyl group may be obtained by acid cleavage of erythromycin-A [See Example 1(a)]. The preparations of α-L-digitoxose and 3-O-methyl-α-L-digitoxose are disclosed by J. S. Brimacombe et al. in *J. Chem. Soc.*, Perkin Trans I, 1982, pp 2583–2487; and the preparations of α-L- and α-L-3-epi-mycarose, α-L-oleandrose, α-L-olivose, α-L-cladinose, α-L-digitoxose and α-L-arcanose as well as the pentoses are disclosed in *The Carbohydrates, Chemistry and Biochemistry*, 1980, 2nd Edition (W. Pigman et al., Editors), Chapter 17 (N. R. William et al.), pp 761–798 Academic Press, N.Y.

Typical suitable starting materials for preparation of the compounds of this invention include any of the known 16-membered macrolides having a free or potentially free hydroxy group at the C-3 carbon as defined in formula I and which may possess other reactive tertiary, secondary or primary hydroxy groups suitably protected as described hereinafter.

Typical suitable starting materials useful in preparation of the compounds of the present invention include the following known antibiotics or those that are readily preparable from known antibiotics. The preparation of desmycosin and that of tylosin are described by R. L. Hamill et al. in U.S. Pat. No. 3,178,341. The preparation of macrocin and that of lactenocin are described by R. L. Hamill et al. in U.S. Pat. No. 3,326,759. Cirramycin A1 is prepared as described by H. Koshiyama et al., *J. Antibiotics Ser.* A16, 59–66 (1963) and S. Nash et al. in U.S. Pat. No. 4,252,898. Antibiotic M-4365 G$_2$ (repromicin) can be prepared by the method described by T. Furumai et al. in *J. Antibiotics*, 30, 443–449 (1977) or as described by A. K. Ganguly in U.S. Pat. No. 3,975,372. The preparation of 9-dihydrodesmycosin (dihydrodesmycosin) is described by E. H. Massey in U.S. Pat. No. 3,769,273. 9-Dihydrolactenocin is prepared in an analogous manner. Rosaramicin can be prepared as described by M. J. Weinstein et al. in U.S. Pat. No. 4,234,690. The preparation of 12,13-deoxo-12,13-dehydrorosaramicin (M-4365A$_2$) and that of 20-deoxo-20-dihydro-12,13-deoxo-12,13-dehydrorosaramicin are described in Examples 1 and 28, respectively, of U.S. Pat. No. 4,056,616. The preparation of 23-demycinosyltylosin (DMT), 20-dihydro-DMT, 5-O-mycaminosyltylonolide (OMT) and of 20-dihydro-OMT are described in U.S. Pat. No. 4,321,361. The preparation of 23-deoxy-5-O-mycaminosyltylonolide (DOMT), 23-de(mycinosyloxy)tylosin (DMOT), 20-dihydrodesmycosin, and of 20-dihydrolactenocin are described in U.S. Pat. No. 4,357,325.

The preparation of 20-deoxo-20-dihydroDMOT is described in U.S. Pat. No. 4,528,369. The production of 16-membered macrolide antibiotics CP-56,064 and CP 56,063 by fermentation of *Streptomyces albus* is described in U.S. Pat. No. 4,454,314.

Other typical suitable starting materials may be prepared from the antibiotics listed hereinabove by use of known synthetic techniques. Thus, for example, the formyl group in desmycosin, DMOT, tylosin, 12,13-deoxo-12,13-dehydrorosaramicin or DMT can be replaced by hydrogen by use of tris(triphenylphosphine) rhodium chloride, in accordance with the procedure described in U.S. Pat. No. 4,345,069, to give the corresponding 19-deformyl derivative, e.g. 19-deformyldesmycosin. In addition, epoxidation of the 12,13 double bond in for example, tylosin, DMT, 19-deformyl DMT, DMOT or 19-deformyl DMOT may be performed using m-chloroperbenzoic acid as described in U.S. Pat. No. 4,477,443 (Examples 58–61) to give the corresponding 12,13-oxo derivative, e.g. 12,13-oxotylosin, 12,13-oxo DMT, 19-deformyl-12,13-oxoDMT, 12,13-oxo DMOT and 19-deformyl-12,13-oxoDMOT. The production of 12,13-oxo DMOT (antibiotic M119a) by fermentation of alkalophilic Actinomycetes is disclosed by H. Tanaba et al. Paper #1150 25th ICAAC, Minneapolis, Minn. 29 Sept. to 2 Oct. 1985.

Additional suitable starting materials useful for preparation of the compounds of this invention may be obtained by modification of the suitable starting materials hereinabove such as 19-deformyl DMT by well known techniques to convert the free hydroxy group at the 23-carbon in such compounds into compounds wherein the 23-carbon is attached to acyloxy-N,N-di(lower alkyl)amino, lower alkoxycarbonyloxy, aralkoxycarbonyloxy, N-loweralkylaminocarbonyloxy or N-aralkylaminocarbonyloxy.

The Glycosylation Reaction

The glycosyl groups are attached to the free hydroxyl group at the C-3 carbon of the 16-membered macrolide starting materials by use of the procedures known in the art. For example, the procedure of Tatsuta, *Carb. Research* 1977, 54, p. 85 or of R. B. Woodward et al., *J. Am. Chem. Soc.* 1981, 103, p. 3215 may be used.

Generally, a suitably protected glycosyl group, e.g., 1-deoxy-1-(pyridyl-2-thio)-α and/or β-L-glycoside such as the 1-S-pyridyl derivative of L-cladinose is reacted with a 16-membered macrolide having a free hydroxyl group at the C-3 carbon (and with other reactive tertiary, secondary and/or primary hydroxyl groups suitably protected) in the presence of anhydrous silver perchlorate or anhydrous silver trifluoromethylsulfonate in an anhydrous aprotic solvent such as acetonitrile. Reaction temperatures of 20°-25° C. for 20-30 hours are conveniently used.

Prior to the glycosylation of the free hydroxy group at the C-3 carbon, any other free hydroxy groups are conveniently protected as acyl derivatives by use of ($C_1$-$C_5$)alkanoic anhydrides, such as, acetic anhydride in the presence of added base such as pyridine, or as the silyl ethers. Standard deprotection techniques which are well known are used to remove the acyl or silyl protecting groups. When the macrolide has a lactone moiety which is sensitive to base-catalyzed ring opening during the deprotecting procedures used to remove, for example, the acyl protecting groups, more labile acyl protecting groups such as aryloxyacyl, haloacetyl, alkoxyacetyl, formyl or haloalkoxycarbonyl may be used. Since very mild basic conditions are employed to remove these more labile acyl groups, the lactone moiety is not adversely affected In this manner, more labile protecting groups such as phenoxyacetyl may be used for protecting the hydroxyl groups in the glycoside group. For example, phenoxyacetyl chloride in the presence of pyridine is reacted with L-digitoxose to form 1,3,4-tri-O-phenoxyacetyl-α- and β-L-digitoxose. The 1-O-phenoxyacetyl group is removed by treatment at ambient temperatures, e.g., 25°C. with aqueous HCL e.g. 0.1N HCl The product so formed is reacted with 2,2-dipyridyldisulfide in the presence of tri-n-butylphosphine to give 3,4-di-O-phenoxyacetyl -1-deoxy1-(pyridyl-2-thio)-α and/or β-L-digitoxose.

Exemplary of the preparation of compounds of the present invention is the following process for the preparation of 3O-α- and/or- β-L-cladinosyl-12,13-deoxo-12,13-dehydrorosaramicin and the corresponding 19-deformyl and 20-deoxo-20-dihydro compounds of formula Ia-c wherein Y=CHO, H and $CH_3$, respectively.

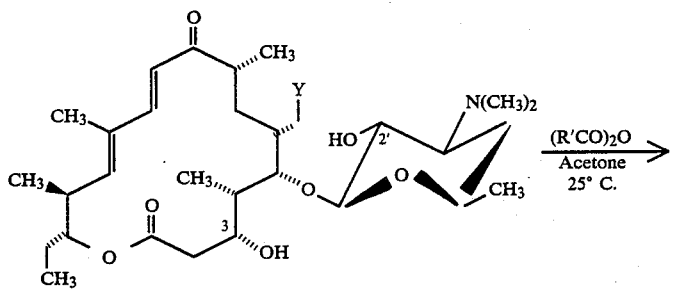

IIIa: Y = CHO
IIIb: Y = H
IIIc: Y = $CH_3$

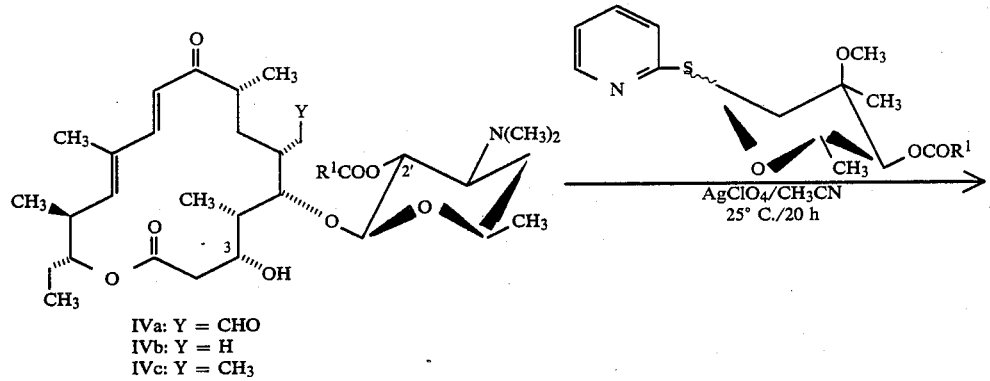

IVa: Y = CHO
IVb: Y = H
IVc: Y = $CH_3$

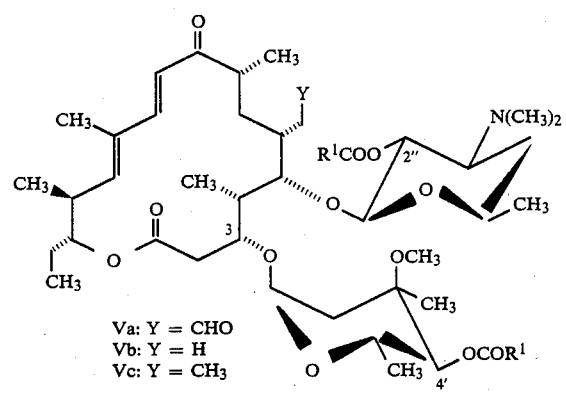

Va: Y = CHO
Vb: Y = H
Vc: Y = $CH_3$

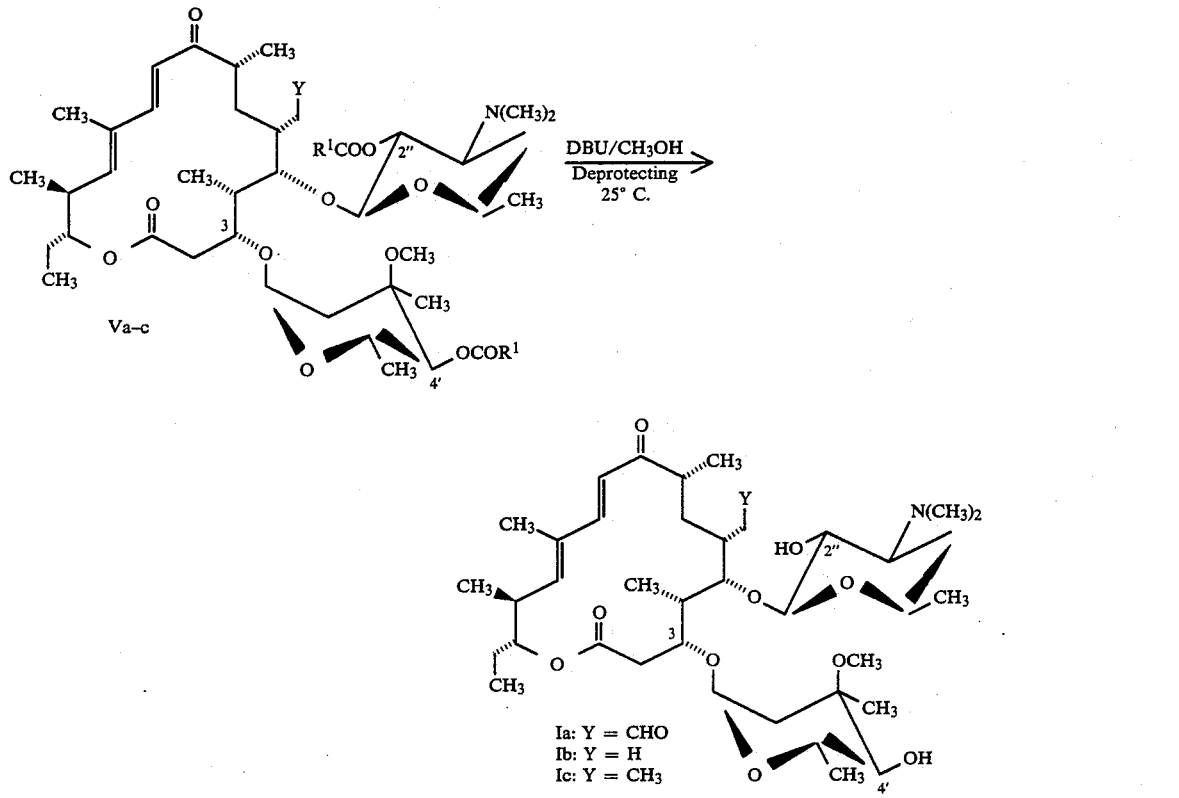

Ia: Y = CHO
Ib: Y = H
Ic: Y = CH₃

As illustrated in the above schematic, 12,13-deoxo-12,13-dehydrorosaramicin or the corresponding 19-deformyl- and 20-deoxo-20-dihydro derivatives represented by formulas IIIa-c wherein Y=CHO, H and CH₃, respectively, is acylated at the hydroxy on the 2' carbon by use of a lower alkanoic acid anhydride, (R'CO)₂O, normally acetic anhydride in acetone at 25° C. to form the 2'-O-acyl 12,13-deoxo-12,13-dehydrorosaramicin represented by formula IVa. Compound IVa is reacted with 4-O-acyl-1-deoxy-1-(pyridyl-2-thio)-α- and/or β-L-cladinoside in the presence of anhydrous silver perchlorate or anhydrous silver trifluoromethylsulfonate in anhydrous acetonitrile at 25° C. for 20 hours to provide the O-(4-O-acyl-α-L-cladinosyl)-(1→3)-12,13-dehydro-12,13-deoxorosaramicin, compound Va (or the corresponding deformyl or 20-deoxo-20-dihydro rosaramicin derivatives) The acyl groups in compound Va-c are removed from the 2" hydroxyl group in the desosaminyl sugar and the 4'-hydroxyl croup in the cladinosyl sugar by treating compound Va-c with an organic trisubstituted nitrogen base for example, 1,8-diazabicyclo[5.4.0]undec-7-ene (DBU) and a lower alkanol, e.g., methanol to give compounds of formula Ia:Y=CHO, Ib: Y=H or Ic:Y=CH₃ and X=Z=H.

As used herein, the term "organic trisubstituted nitrogen base" refers to acyclic tertiary amines, pyridine and lower alkyl substituted pyridines and bicyclic tertiary amines. Typical suitable acyclic tertiary aliphatic amines include tri(lower alkyl) amines such as trimethylamine, triethylamine, tri-n-propylamine and dimethyl-sec-butylamine. Triethylamine is the preferred acyclic tertiary amine Typical suitable substituted pyridines include 2-, 3- and 4-methylpyridine. Typical suitable bicyclic tertiary amines include 1,5-diazabicyclo[4.4.0]non-5-ene, hereinafter "DBN" and 1,8-diazabicyclo[5.4.0]undec-7-ene, hereinafter "DBU".

The term "lower alkanol" refers to straight and branched-chain alcohols of one to six carbons such as methanol, ethanol, n- and iso-propanol. Methanol is preferred.

The 4-O-acylcladinosyl derivatives (VIa-c) of the compounds of formulas Ia-c are prepared by selectively removing the acyl group from the 2" position of the desosaminyl sugar by treating compounds Va-c with a lower alkanol, normally methanol, at 25° C. for 16 hours.

Va-c $\xrightarrow{\text{CH}_3\text{OH}}_{25° \text{C}}$

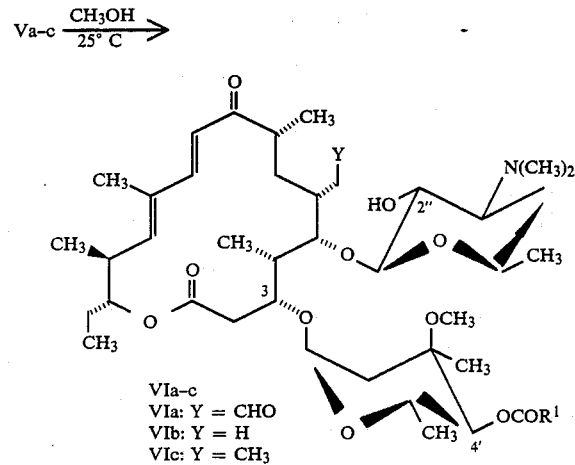

VIa-c
VIa: Y = CHO
VIb: Y = H
VIc: Y = CH₃

Using procedures similar to those outlined for the preparation of 3-O-α-glycosyl 16-membered macrolide antibacterials of this invention, the 3-O-β-glycosyl 16- membered macrolide antibacterials of this invention wherein the glycosyl group, $R_1$, is represented by formula II may be prepared as described in Example 20.

The 3-O-glycosyl 16-membered macrolide antibacterials of this invention wherein the glycosyl croup, $R_1$, is represented by the formula IIA may be prepared as described in Example 18.

This invention also relates to a pharmaceutical composition comprising a compound of the present invention or its pharmaceutically acceptable acid addition salts in admixture with a pharmaceutically acceptable carrier.

The compounds of the present invention are capable of forming pharmaceutically acceptable acid addition salts with inorganic and organic acids. The term "pharmaceutically acceptable acid addition salts" means those salts that do not exhibit toxic manifestations at normal therapeutic doses. Exemplary of such salts are those formed by reaction of the compounds of this invention with acids such as hydrochloric, sulfuric, phosphoric, citric, acetic, propionic, tartaric, maleic, benzoic, cyclopropylcarboxylic, adamantylcarboxylic, lauryl sulfonic, glucoheptonic, stearic, lactobionic and the like. Pharmaceutically acceptable acid addition salts may be prepared by methods generally used in the art such as by adding a stoichiometric amount of acid to a solution of a compound of the invention in an inert organic solvent and isolating the salt by art known methods such as precipitation of the salt with a solvent wherein the salt is not appreciably soluble, e.g. diethyl ether. An inert organic solvent is one which does not react with the antibacterial, the acid or the salt under conditions of the reaction.

Typical pharmaceutically acceptable carriers suitable for use in the formulations described are exemplified by sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants, ethylene glycol polymers; betacyclodextrin; fatty acids, hydrolyzed cereal solids; water, polyalkylene glycols; gums; and petroleum ; as well as other non-toxic compatible fillers, binders, and lubricants commonly used in pharmaceutical formulations. The compositions may also contain preservatives, areosol propellants and coloring, thickening, suspending, dispensing, emulsifying, wetting, stabilizing and buffering agents.

This invention also embraces a method of eliciting an antibacterial effect against susceptible bacterial infections which comprises administering to an animal, preferably a warm-blooded animal such as man having a susceptible bacterial infection an antibacterially effective amount of a compound of formula I or a pharmaceutical composition thereof In order to elicit an antibacterial effect against a susceptible bacterial infection, the compounds of this invention may be administered orally, intramuscularly, topically or intraveneously. Administration may be effected by any of the conventional methods, i.e., by the use of tablets, capsules, and suspensions, solutions, creams, ointments or injectables Each of the dosage forms can be formulated utilizing non-toxic pharmaceutically acceptable excipients conventionally known in the art. The compounds of this invention are preferably administered intravenously at doses of from about 5 to about 50 mg per kg per day, preferably from about 15 to about 30 mg per kg per day, in single or divided doses. The compounds of this invention may also be administered orally at doses of from about 15 mg/kg to 50 mg/kg or subcutaneously at doses of about 15 mg/kg to 30 mg/kg.

The compounds of this invention elicit an antibacterial effect against a wide variety of bacterial species, but are generally more active against strains of Gram-positive bacteria. Exemplary of the bacteria against which the compounds of this invention are active are various strains of *Staphylococci* and *Streptococci*.

The compounds of the invention have enhanced (IV) serum levels and a similar spectrum of antibacterial activity to that of the corresponding parent 16-membered macrolide having a free C-3 hydroxyl group. The compounds are also active against erythromycin-resistant strains of *Staphylococci* and methicillin-susceptible and methicillin-resistant strains of *Staphylococci*.

Specifically,O-($\alpha$-L-cladinosyl)-(1→3)-12,13-dihydro-12,13-deoxorosaramicin, a compound of this invention compared to 12,13-dehydro-12,13-deoxorosaramicin, is slightly less active against erythromycin-resistant strains of *Staphylococci* and against sensitive Gram-positive bacteria, but equal to, or slightly more active against various strains of *Streptococci*.

The antibacterial activity of the compounds of this invention is determined by testing against a variety of pathogens using standard antibacterial dilution assays in Mueller-Hinton agar, the activity being expressed as the Minimum Inhibitory Concentration (MIC, mcg./ml., 24 hours). The geometric mean MIC's of the compounds of this invention are in the range of about 0.088 to 27.

Most importantly, the compounds of this invention are active antibacterial agents which afford good serum levels at the antibacterially effective dosages provided hereinabove.

EXAMPLE 1

4-O-Acetyl-1-Deoxy-1-(Pyridyl-2-thio)-$\alpha$- and -$\beta$-L-Cladinoside (a) L-Cladinose Erythromycin A (Merck Index, 10th Edition Entry No. 3624) (50g) was dissolved in 1N aqueous hydrochloric acid (70 mL) and water (500 mL) and the mixture subjected to liquid-liquid extraction using diethyl ether for 99 h. The ether extract was evaporated to dryness to give L-cladinose (11.7 g, 97%) as a colorless viscous oil.

(b) 1,4-Di-Oacetyl-$\beta$-L-cladinose

L-Cladinose (16.23 g) and acetic anhydride (66.7 mL) were dissolved in dry pyridine (133 mL) and the mixture was allowed to remain at 25° C. for 18 h. The mixture was evaporated to dryness and the residue was azeotroped with toluene. The product was chromatographed on a silica gel column (45×5 cm) using 3% ethyl acetate in chloroform (v/v) as the eluant to give 1,4-di-O-acetyl-$\beta$-L-cladinose (19.2 g, 80%) as a colorless solid (Anal. found: C,55.79; H, 7.91%; $C_{12}H_{20}O_6$ requires: C, 55.37; H, 7.74%); MS: 201 (MH+-CH$_3$COO); Rotation: $[\alpha]_D^{26}$ −41.3° (CHCl$_3$); IR: $\nu_{max}$ (CDCl$_3$) 1750, 1735, 1238, 1050 cm$^{-1}$; 'H-NMR: $\delta_H$ (CDCl$_3$) 1.17 (3H,d,J$_{5ax,6\text{-}CH3}$ 7 Hz, 6-CH$_3$), 1.17 (3H,s,3-CH$_3$), 1.57 (1H,dd,J$_{1ax,2ax}$ 10 Hz, J$_{2ax,2eq}$ 13 Hz H$_{2ax}$), 2.12 (3H,s,1-OCOCH$_3$), 2.15 (3H,s,4-OCOCH$_3$), 2.28 (1H,dd,J$_{1ax,2eq}$ 2 Hz,J$_{2ax,2eq}$ 13 Hz,H$_{2eq}$ 3.32 (3H,s,3-OCH$_3$), 4.10 (1H,dq,J$_{5ax,6\text{-}CH3}$ 7 Hz, J$_{4ax,5ax}$ 10 Hz, H$_{5ax}$), 4.68 (1H,d,J$_{4ax,5ax}$ 10 Hz,H$_{4ax}$) and 5.92 (1H,dd,J$_{1ax,2ax}$ 10 Hz, J$_{1ax,2eq}$ 2 Hz, H$_{1ax}$).

(c) 4-O-Acetyl-α- and -L-cladinose 1,4-Di-O-actyl-β-L-cladinose (2.18 g) was dissolved in 0.1N aqueous hydrochloric acid (245 mL) and the mixture was allowed to remain at 25° C. for 1 h. The mixture was extracted with diethyl ether and the ether layer was retained. The aqueous acid layer was neutralized and extracted with dichloromethane. The latter was combined with the ether extract and dried (MgSO$_4$), filtered and evaporated to dryness to give 4-O-acetyl-α- and β-L-cladinose (1.86 g, 100%) as a colorless gum that was used without further purification.

(d) 4-O-Acetyl-1-deoxy-1-(pyridyl-2-thio)-α- and -β-L-cladinoside

4-O-Acetyl-L-cladinose (1.84 g) was dissolved in dry dichloromethane (25 mL) and the solution was cooled to 13° C. After 30 minutes a chilled solution of 2,2'-dipyridyldisulphide (Aldrithiol-2) (2.8 g) and tri-n-butylphosphine (3.45 g) in dry dichloromethane (30 mL) was added in one portion. The mixture was allowed to remain at 13° C. under dry argon for 19 h. The solution was evaporated to dryness and the residue chromatographed twice on silica gel columns (20×5 cm) using first 4% ethyl acetate in chloroform and then 2% ethyl acetate in chloroform (v/v) as the eluant to give 4-O-acetyl-1-deoxy-1-(pyridyl-2-thio)-α-L-cladinoside (604 mg, 23%) as a colorless gum (Anal.: found: C, 58.15; H, 6.84; N, 4.54% C$_{15}$H$_{21}$NO$_4$S requires: C, 57.86; H, 6.80; N, 4.50%); MS: m/z 312 (MH$^+$); Rotation: [α]$_D^{26}$ −339.0° (CHCl$_3$); UV: λ$_{max}$ (CF$_3$CH$_2$OH) 239 nm (ε9,029), 282 nm (ε5,122); IR: ν$_{max}$ (CDCl$_3$) 1730, 1580, 1418, 1238, 1063, 1045 cm$^{-1}$; $^1$H-NMR: δ$_H$(CDCl$_3$) 1.12 (3H,d,J$_{5ax,6\text{-}CH3}$ 7 Hz, 6-CH$_3$), 1.20 (3H,s,3-CH$_3$), 2.15 (1H,dd,J$_{1eq,2ax}$ 5 Hz, J$_{2eq,2ax}$15 Hz,H$_{2ax}$), 2.17 (3H,s,4-OCOCH$_3$), 2.58 (1H,dd,J$_{1eq,2eq}$ 2 Hz, J$_{2eq,2ax}$ 15 Hz, H$_{2eq}$), 3.37 (3H,s,3-OCH$_3$), 4.53 (1H,dg,J$_{5ax,6\text{-}CH3}$ 7 Hz, J$_{4ax,5ax}$ 10 Hz, H$_{5ax}$) 4.74 (1H,d,J$_{4ax,5ax}$ 10 Hz, H$_{4ax}$), 6.38 (1H, dd, J$_{1eq,2eq}$ 2 Hz, J$_{1eg,2ax}$ 5 Hz, H$_{1eg}$), 7.00 (1H, m, 1-S-C$_5$H$_4$N(H$_5$)), 7.33 (1H,m, 1-S-C$_5$H$_4$N(H$_3$)), 7.52 (1H, m, 1-S-C$_5$H$_4$(H$_4$)) and 8.51 (1H, m, 1-S-C$_5$H$_4$N(H$_6$)), and 4-O-acetyl-1deoxy-1-(pyridyl-2thio)-β-L-cladinoside (12) (1.02 g, 39%) as a colourless gum (Anal.: found: C, 57.46; H, 6.86; N, 4.36. C$_{15}$H$_{21}$NO$_4$S requires: C, 57.86; H, 6.80; N, 4.50%); MS: m/z 312 (MH$^+$); Rotation: [α]$_D^{26}$ −1.1° (CHCl$_3$); UV: λ$_{max}$ (CF$_3$CH$_2$OH) 237 nm (ε7,814), 279 nm (ε4,585); IR: ν$_{max}$ (CDCl$_3$) 1737, 1580, 1418, 1238, 1072, 1046 cm$^{-1}$; $^1$H-NMR: δ$_H$ (CDCl$_3$) 1.16 (3H,d,J$_{5ax,6\text{-}CH3}$ 7 Hz,6-CH$_3$), 1.19 (3H, s, 3-CH$_3$), 1.81 (1H, dd, J$_{1ax,2ax}$ 11 Hz, J$_{2eq,2ax}$ 16 Hz, H$_{2ax}$), 2.16 (3H, s, 4-OCOCH$_3$), 2.44(1H, dd, J$_{1eq,2eq}$ 2 Hz, H$_{2eq,2ax}$ 16 Hz, H$_{2eq}$), 3.34 (3H, s, 3-OCH$_3$), 4.12 (1H, dg, J$_{5ax,6\text{-}CH3}$ 7 Hz, J$_{4ax,5ax}$ 10 Hz, H$_{5ax}$), 4.73 (1H, d, J$_{4ax,5ax}$, 10 Hz, H$_{4ax}$), 5.70 (1H, dd, J$_{1ax,2ax}$ 11 Hz, J$_{1ax,2eq}$ 2 Hz, H$_{1ax}$), 7.06 (1H, m, 1-S-C$_5$H$_4$N(H$_5$)), 7.35 (1H, m, 1-S-C$_5$H$_4$N(H$_3$)), 7.56 (1H, m, 1-S-C$_5$H$_4$N(H$_4$)) and 8.42 (1H, m, 1-S-C$_5$H$_4$N(H$_6$)).

EXAMPLE 2

O-α-L-Cladinosyl-(1→3)-12,13-dehydro-12,13-deoxorosaramicin (a) 2'-O-Acetyl-12,13-dehydro-12,13-deoxorosaramicin 12,13=Dehydro-12,13-deoxorosaramicin (2 g) and acetic anhydride (1 mL) were dissolved in dry acetone (100 mL) and the solution so formed was allowed to remain at 25° C. for 19 h. The reaction mixture was evaporated to dryness and the residue was taken up in dichloromethane and washed with water having a oH equal to 10. The organic layer was dried (MgSO$_4$), filtered and evaporated to dryness. The residue was chromotographed on a silica gel column (60×2 cm) using 10% acetone in chloroform as the eluant to give 2'-O-acetyl-12,13-dehydro-12,13-deoxorosaramicin (1.79 g, 83%) as a colorless amorphous solid (Anal.: found: C, 62.06; H, 8.34; N, 1.54%; C$_{33}$H$_{53}$NO$_9$ 0.2 CHCl$_3$ requires: C, 62.75; H, 8.46; N, 2.22%); MS: m/z 608 (MH$^+$); Rotation: [α]$_D^{26}$−4.4° (CHCl$_3$; UV: λ$_{max}$ (CF$_3$CH$_2$OH) 288 nm (ε19,165); IR: ν$_{max}$(CDCl$_3$) 3530, 1740, 1723, 1675, 1593, 1248, 1060 cm$^{-1}$; $^1$H-NMR: δ$_H$ (CDCl$_3$) 0.93 (3H,t,J$_{16,17\text{-}CH3}$ 7 Hz, 17-CH$_3$), 0.96 (3H,d,J 7 Hz, CH$_3$), 1.08 (3H,d,J 7 Hz, CH$_3$), 1.20 (3H,d,J,7 Hz,CH$_3$), 1.22 (3H,d,J,7 Hz,CH$_3$), 1.81 (3H,d,J$_{12\text{-}CH3}$,$^{13}$ 1 Hz, 12-CH$_3$), 2.08 (3H,s,2'-OCOCH$_3$), 2.26 (6H,s,3'-(CH$_3$)$_2$), 4.25 (1H,d,J$_{1ax,2'ax}$ 8 Hz, H$_{1'ax}$), 5.66 (1H,dq,J$_{12\text{-}CH,13}$ 1 Hz, J$_{13,14}$ 10 Hz, H$_{13}$), 6.30 (1H,d,J$_{10,11}$ 16 Hz, H$_{10}$), 7.31 (1H,d,J$_{10,11}$ 16 Hz, H$_{11}$) and 9.70 (1H,s,H$_{20}$).

(b) 2''-O-Acetyl-O-(4'-O-acetyl-α-L-cladinosyl)-(1→3)-12,13-dehydro-12,13-deoxorosaramicin 2'-O-Acetyl-12,13-dehydro-12,13deoxorosaramicin (1 g) and 4-O-acetyl-1-deoxy-1-(pyridyl-2-thio)-α- and -β-L-cladinoside (from Example I(d)) (2.83 g) were dissolved in dry acetonitrile (60 mL) under dry argon. A solution of anhydrous silver perchlorate (2.22 g) in dry acetonitrile (61 mL) was added and the mixture was stirred under dry argon at 25° C. for 18 h. The mixture was evaporated to dryness and the residue was taken up in dichloromethane and washed with water, the pH being adjusted to 10. The organic layer was dried (MgSO$_4$), filtered and evaporated to dryness. The residue was chromatographed on a silica gel column (30×5 cm) using ethyl acetate as the eluant to give unreacted 2'-O-acetyl-12,13-dehydro-12,13-deoxorosaramicin (460 mg., 46%) and 2''-O-acetyl-O-(4'-O-acetyl-α-L-cladinosyl)-(1→3)-12,13-dehydro-12,13-deoxorosaramicin (718 mg., 54%) as a colorless amorphous solid (Anal.: found: C, 62.30; H, 8.27; N, 1.53%; C$_{43}$H$_{69}$NO$_{13}$. 0.2 CHCl$_3$ requires: C, 62.08; H, 8.36; N, 1.68%); MS: m/z 808 (MH$^+$); Rotation: [α]$_D^{26}$ −46.5° (CHCl$_3$); UV: λ$_{max}$ (CF$_3$CH$_2$OH) 287 nm (ε17,964); IR: ε$_{max}$ (CDCl$_3$) 1737, 1728, 1673, 1590, 1242, 1050 cm$^{-1}$; $^1$H-NMR: δ$_H$ (CDCl$_3$) 0.89 (3H,t,J$_{16,17\text{-}CH3}$ 7 Hz, 17-CH$_3$), 0.94 (3H,d,J 7 Hz, CH$_3$), 1.04 (3H,s,3'-CH$_3$), 1.05 (3H,d,J 7 Hz,CH$_3$), 1.06 (3H,d,J 7 Hz, CH$_3$), 1.18 (3H,d,J 7 Hz, CH$_3$), 1.20 (3H,d,J 7 Hz, CH$_3$), 1.79 (3H,d,J$_{12\text{-}CH3}$,13 1 Hz, 12-CH$_3$), 2.08 (3H,s,2''-OCOCH$_3$), 2.11 (3H,s,4'-OCOCH$_3$), 2.29 (6H,s,3''-N(CH$_3$)$_2$), 3.17 (3H,s,3'-OCH$_3$), 4.33 (1H,d,J$_{1''ax,2''ax}$ 8 Hz, H$_{1''ax}$), 4.66 (1H,d,J$_{4'ax,5'ax}$ 10 Hz, H$_{4'ax}$), 4.74 (1H,dd,J$_{1''ax,2''ax}$ 8 Hz, J$_{2''ax,3''ax}$ 10 Hz, H$_{2''ax}$), 4.99 (1H,dd,J$_{1'eq,2'eq}$ 1.5 Hz, J$_{1'eq,2'ax}$ 4 Hz, H$_{1'eq}$), 5.64 (1H,dg, J$_{12\text{-}CH3'}{13}$1 Hz, J$_{13,14}$ 10 Hz, H$_{13}$), 6.25

(1H,d,J$_{10,11}$ 16 Hz, H$_{10}$), 7.28 (1H,d,J$_{10,11}$ 16 Hz, H$_{11}$) and 9.71 (1H,s,H$_{20}$).

(c) O-α-L-Cladinosyl-(1→3)-12,13-dehydro-12,13-deoxorosaramicin

2''-O-Acetyl -O-(4'-O-acetyl-α-L-cladinosyl)(1→3)-12,13-dehydro-12,13-deoxorosaramicin (567 mg) was dissolved in a 0.57% (w/v) solution of 1,8-diazabicyclo[5.4.0]undec-7-ene (0.1065 mL) in methanol (19 mL) and the solution was stirred at 25° C. under argon for 43 h. The mixture was evaporated to dryness and the residue was taken up in dichloromethane and washed with water, the pH being adjusted to 10. The organic layer was dried (MgSO$_4$), filtered and evaporated to dryness. The residue was chromotographed on a silica gel column (15×5 cm) using 2.5% methanol in chloroform as the eluant to give O-α-L-cladinosyl-(1→3)-12,13-dehydro-12,13-deoxorosaramicin (265 mg., 52%) as a colourless amorphous solid (Anal.: found: C, 64.19; H, 9.46; N, 2.01%; C$_{39}$H$_{65}$NO$_{11}$ requires: C, 64.71; H, 9.05; N, 1.93%); MS: m/z 724 (MH$^+$); Rotation: [α]$_D^{26}$ −51.0° (CHCl$_3$); UV: λmax (CH$_3$OH) 282 nm (ε19,623); IR: $\nu_{max}$ (CDCl$_3$) 3540, 3440, 1728, 1674, 1590, 1160, 1050 cm$^{-1}$; $^1$H-NMR: δ$_H$(CDCl$_3$) 0.90 (3H,t,J$_{16,17}$-CH$_3$ 7 Hz, 17-CH$_3$), 1.05 (3H,d,J 7 Hz, CH$_3$), 1.11 (3H,d,J 7 Hz, CH$_3$), 1.15 (3H,s,3'-CH$_3$), 1.17 (3H,d,J 7 Hz, CH$_3$), 1.19 (3H,d,J 7 Hz, CH$_3$), 1.20 (3H,d,J 7 Hz, CH$_3$), 1.79 (3H,d,J$_{12}$-CH$_3$'$_{13}$ 1 Hz, 12-CH$_3$), 2.28 (6H,s,3''-N(CH$_3$)$_2$), 3.12 (3H$_s$,3'-OCH$_3$), 4.24 (1H,d,J$_{1''ax,2''ax}$ 8 Hz, H$_{1''ax}$), 4.67 (1H,m,H$_{15}$), 4.94 (1H,dd,J$_{1'eq,2'eq}$ 1 Hz, J$_{1'eq,2'ax}$ 4Hz, H$_{1'eq}$), 5.67 (1H,dq,J$_{12}$-CH$_{3'}$, $_{13}$ 1 Hz, J$_{13,14}$ 10 Hz, H$_{13}$), 6.24 (1H,d,J$_{10,11}$ 16 Hz, H$_{10}$), 7.33 (1H,d,J$_{10,11}$ 16 Hz, H$_{11}$) and 9.75 (1H,s,H$_{20}$).

EXAMPLE 3

O-α-L-Cladinosyl-(1→3)-12,13-dehydro-12,13,20-dideoxo-20-dihydrorosaramicin

(a) 2'O-Acetyl-12,13-dehydro-12,13,20-dideoxo-20-dihydrorosaramicin 12,13-Dehydro-12,13,20-dideoxo-20-dihydrorosaramicin (prepared as described in Example 28 of U.S. Pat. No. 4,056,616) (4 g) was dissolved in dry acetone (167 mL) and acetic anhydride (2.05 mL) was added. The mixture was stirred at 25° C. for 18 h under dry argon. The solution was evaporated to dryness and the residue was taken up in dichloromethane and washed with water, the pH being adjusted to 10. The organic layer was dried (MgSO$_4$), filtered and evaporated to dryness. The residue was chromatographed on a silica gel column (60×2.5 cm) using 10% acetone in chloroform (v/v) as the eluant to give 2'-O-acetyl-12,13-dehydro-12,13,20-dideoxo-20-dihydrorosaramicin (3.7c, 85%) as a colourless amorphous solid (Anal.: found: C, 65.14; H, 9.04; N, 2.19%; C$_{33}$H$_{55}$NO$_8$.0.1 CHCl$_3$ requires: C, 65.43; H, 9.15; N, 2.31%); MS: m/z 594 (MH$^+$); Rotation [α]$_D^{26}$ +7.9° (CHCl$_3$); UV: λ$_{max}$ (CF$_3$CH$_2$OH) 287 nm (ε21,705); IR: $\nu_{max}$(CDCl$_3$) 3310, 1737, 1725, 1677, 1592, 1250, 1188, 1060 cm$^{-1}$; $^1$H-NMR: δ$_H$(CDCl$_3$) 0.85 (3H,t,J$_{16,17}$-CH$_3$ 7 Hz, 17-CH$_3$), 0.94 (3H,t,J$_{19,20}$-CH$_3$ 7 Hz, 20-CH$_3$), 0.99 (3H,d,J 7 Hz, CH$_3$), 1.20 (3H,d,J 7 Hz, CH$_3$), 1.08 (3H,d,J 7 Hz, CH$_3$), 1.22 (3H,d,J 7 Hz, CH$_3$), 1.79 (3H,d,J$_{12}$-CH$_{3,13}$ 1 Hz, 12-CH$_3$), 2.09 (3H,s,2'-OCOCH$_3$), 2.27 (6H,s,3'-N(CH$_3$)$_2$), 3.46 (1H,m,H$_{5'ax}$), 3.72 (1H,dd,J$_{4,5}$ 10 Hz, J$_{5,6}$ 1 Hz, H$_5$), 4.33 (1H,d,J$_{1'ax,2'ax}$ 8 Hz, H$_{1'ax}$), 4.70 (1H,m,H$_{15}$), 4.80 (1H,dd,J$_{1'ax,2'ax}$ 8 Hz, J$_{2'ax,3'ax}$ 10 Hz, H$_{2'ax}$), 5.64 (1H,dg,J$_{12}$-CH$_{3,13}$ 1 Hz, J$_{13,14}$ 10 Hz, H$_{13}$), 6.33 (1H,d,J$_{10,11}$ 16 Hz, H$_{10}$) and 7.32 (1H,d,J$_{10,11}$ 16 Hz, H$_{11}$).

(b) 2''-O-Acetyl-O-(4'-O-acetyl-α-L-cladinosyl)-(1→3)-12,13-dehydro-12,13-dehydro-12,13,20-dideoxo-20-dihydrorosaramicin 2'-O-Acetyl-12,13-dehydro-12,13,20-dihydrorosaramicin (1.57 g) and 4-O-acetyl-1-deoxy-1-(pyridyl-2-thio)-α and -β-L-cladinoside (Example 1(d)) (4.55 g) were dissolved in dry acetonitrile (111 mL) under dry argon. A solution of anhydrous silver perchlorate (3.61 g) in dry acetonitrile (100 mL) was added and the mixture was stirred under dry argon at 25° C. for 26 h. The solution was evaporated to dryness and the residue was taken up in dichloromethane and washed with water, the pH being adjusted to 10. The organic layer was dried (MgSO$_4$), filtered and evaporated to dryness. The residue was chromatographed on a silica gel column (30×5 cm) using ethyl acetate as the eluant to give unreacted 2'-O-acetyl-12,13-dehydro-12,13,20-dideoxo-20-dihydrorosaramicin (471 mg., 30%) and 2''-O-acetyl-O-(4'-O-acetyl-α-L-cladinosyl)-(1→3)-12,13-dehydro-12,13,20-dideoxo-20-dihydrorosaramicin (1.31 g, 63%) as a colorless amorphous solid (Anal.: found: C, 60.51; H, 8.26; N, 1.22%; C$_{43}$H$_{71}$NO$_{12}$. 0.5 CHCl$_3$ requires: C, 60.50; H, 8.38; N, 1.64%); MS: m/z 794 (MH$^+$); Rotation: [α]$_D^{26}$ −91.2° (CHCl$_3$); UV: λ$_{max}$ (CF$_3$CH$_2$OH) 286 nm (ε19,336), IR: $\nu_{max}$(CDCl$_3$) 1733, 1673, 1591, 1240, 1160, 1048 cm$^{-1}$; $^1$H-NMR: δ$_H$ (CDCl$_3$)
0.89 (3H,t,J$_{16,17}$-CH$_3$ 7 Hz, 17-CH$_3$), 0.90 (3H,t,J$_{19,20}$-CH$_3$ 7 Hz, 20-CH$_3$), 0.96 (3H,d,J$_{4,4}$-CH$_3$ 7 Hz, 14-CH$_3$), 1.03 (3H,d,J$_{14,14}$-CH$_3$ 7 Hz, 14-CH$_3$), 1.04 (3H,s,3'-CH$_3$), 1.09 (3H,d,J$_{5''ax,6''}$-CH$_3$ 7 Hz, 6''-CH$_3$), 1.18 (3H,d,J$_{8,8}$-CH$_3$ 7 Hz, 8-CH$_3$), 1.18 (3H,d, J$_{5''ax,6''}$-CH$_3$ 7 Hz, 6''-CH$_3$), 1.78 (3H,d,J$_{12}$-CH$_{3,13}$ 1 Hz, 12-CH$_3$), 2.08 (3H,s,2''-OCOCH$_3$), 2.12 (3H,s,4'-OCOCH$_3$), 2.28 (6H,s,3''-N(CH$_3$)$_2$), 3.19 (3H,s,3'-OCH$_3$), 3.51 (1H,m,H$_{5''ax}$), 3.69 (1H,dd,J$_{4,5}$ 10 Hz, J$_{5,6}$ 1 Hz, H$_5$), 4.36 (1H,d,J$_{1''ax,2''ax}$ 8 Hz, H$_{1''ax}$), 4.63 (1H,m,H$_{15}$), 4.65 (1H,d,J$_{4'ax,5'ax}$ 10 Hz, H$_{4'ax}$), 4.74 (1H,dd,J$_{1''ax,2''ax}$ 8 Hz, J$_{2''ax,3''ax}$ 10 Hz, H$_{2''ax}$), 4.85 (1H,dd,J$_{1'eq,2'eq}$ 1.5 Hz, J$_{1'eq,2'ax}$ 4 Hz, H$_{1'eg}$), 5.59 (1H,dg,J$_{12}$-CH$_{3,13}$ 1 Hz, J$_{13,14}$ 10 Hz, H$_{13}$), 6.23 (1H,d,J$_{10,11}$ 16 Hz, H$_{10}$) and 7.23 (1H,d,J$_{10,11}$ 16 Hz, H$_{11}$).

The proton assignments were confirmed by means of a 2-D-NMR experiment at 400 MHz (δ$_H$/J correlation).

O-α-L-Cladinosyl-(1→3)-12,13-dehydro-12,13,20-dideoxo-20-dihydrorosaramicin

2''-O-Acetyl-O-(4'-O-acetyl-α-L-cladinosyl-(1→3)-12,13-dehydro-12,13,20-dideoxo-20-dihydrorosaramicin (750 mg) and 1,8-diazabicyclo[5.4.0]undec-7-ene (0.705 mL) were dissolved in methanol (25 mL) and the solution was stirred at 25° C. for 20 h. The mixture was evaporated to dryness and the residue was taken up in dichloromethane and washed with water, the pH being adjusted to 10. The organic layer was dried (MgSO$_4$), filtered and evaporated to dryness. The residue was chromatographed on a silica gel column (60×2 cm) using 2% methanol in chloroform (v/v) as the eluant. The product was rechromatographed on a silica gel column (15×2 cm) using first chloroform (1 L) and then 2.5% increasing to 10% methanol in chloroform (v/v) as the elueant to give O-α-L-cladinosyl-(1→3)-12,13-dehydro-12,13,20-dideoxo-20-dihydrorosaramicin (428 mg., 64%) as a colorless amorphous solid. (Anal.: found: C, 61.55; H, 8.78; N, 1.56%; C$_{39}$H$_{67}$NO$_{10}$.0.4 CHCl$_3$ requires: C, 61,82; H, 8.91; N, 1.85%); MS: m/z 710 (MH$^+$); Rotation: [α]$_D^{26}$ −47.2° (CHCl$_3$); UV: λ$_{max}$ (CH$_3$OH) 282 nm (ε20,594); IR: $\nu_{max}$(CDCl$_3$) 3550, 3440, 1730, 1670, 1590, 1160, 1055, 1020 cm$^{-1}$; $^1$H-MR: δ$_H$ (CDCl$_3$) 0.89 (3H,t,J$_{16,17}$-CH$_3$ 7

Hz, 17-CH₃), 0.93 (3H,t,J₁₉,₂₀-CH₃ 7 Hz, 20-CH₃), 1.04 (3H,d,J 7 Hz, CH₃), 1.13 (3H,d,J 7 Hz, CH₃), 1.15 (3H,s,3'-CH₃), 1.18 (3H,d,J 7 Hz, CH₃), 1.20 (3H,d,J 7 Hz, CH₃), 1.24 (3H,d,J 7 Hz, CH₃), 1.78 (3H,d,J₁₂-CH₃,13 1 Hz, 12-CH$_{CH3}$), 2.28 (6H,s,3''-(CH₃)₂), 3.14 (3H,s,3'-OCH₃), 4.26 (1H,d,J₁''ax,2''ax 8 Hz, H₁''ax), 4.64 (1H,m,H₁₅), 4.81 (1H,dd,J₁'eq,2'eq 1 Hz, J₁'eq,2'ax 4 Hz, H₁'eq), 5.62 (1H,dg,J₁₂-CH₃,13 1 Hz, J₁₃,₁₄ 10 Hz, H₁₃), 6.23 (1H,d,J₁₀,₁₁ 16 Hz, H₁₀) and 7.28 (1H,d,J₁₀,₁₁ 16 Hz, H₁₁).

EXAMPLE 4

2'',4'',4''''-Tri-acetyl-O(4'-acetyl-α-L-cladinosyl)(a)

(a) 2',4',4''-Tri-α-acetyldesmycosin

Desmycosin (Merck Index, Tenth Edition, p. 1405) (3.6 g) and acetic anhydride (1.54 mL) were dissolved in dry pyridine (150 mL) and the mixture was allowed to remain at 25° C. for 74 h. The mixture was evaporated to dryness and the residue was azeotroped with toluene. The residue was chromatographed on a silica gel column (30×5 cm) using 15% acetone in chloroform as the eluant to give 2',4',4''-tri-O-acetyldesmycosin (1.91 g., 46%) as a colorless amorphous solid. (Anal.: found: C, 60.09; H, 8.08; N, 1.44%; C₄₅H₇₁NO₁₇ requires: C, 60.18; H, 7.97; N, 1.56%); MS: m/z 898 (MH⁺); Rotation: $[α]_D^{26}$ −3.1° (CHCl₃); UV: λ$_{max}$ (CF₃CH₂OH) 286 nm (ε22,009); IR: ν$_{max}$ (CDCl₃) 3530, 1740, 1678, 1593, 1235, 1167, 1050 cm⁻; ¹H-NMR: δ$_H$(CDCl₃) 0.93 (3H,t,J₁₆,₁₇-CH₃ 7 Hz, 17-CH₃), 0.97 (3, d,J 7 Hz, CH₃), 1.14 (3H,d,J 7 Hz, CH₃), 1.18 (3H,d,J 7 Hz, CH₃), 1.22 (3H,d,J 7 Hz, CH₃), 1.80 (3H,d,J₁₂-CH13 1 Hz, 12-CH₃), 2.05 (3H,s,4'-OCOCH₃), 2.06 (3H,s,2'-OCOCH₃) 2.12 (3H,s,4''-OCOCH₃), 2.34 (6H,s,3'-(CH₃)₂), 3.50 (3H,s,2''-OCH₃), 3.54 (3H,s,3''OCH₃), 4.33 (1H,d,J₁'ax,2'ax 8 Hz, H₁'ax), 4.66 (1H,d,J₁''ax,2''ax 8 Hz, H₁''ax), 5.94 (1H,dq,J₁₂-CH₃,13 1 Hz, J₁₃,₁₄ 10 Hz, H₁₃), 6.32 (1H,d,J₁₀,₁₁ 16 Hz, H₁₀), 7.36 (1H,d,J₁₀,₁₁ 16 Hz, H₁₁), and 9.71 (1H,s,H₂₀).

(b) 2'',4'',4''''-Tri-O-acetyl-O-(4'—C-acetyl-α-L-cladinosyl)-(1→3)-desmycosin

2',4',4''-Tri-O-acetyldesmycosin (335 mg) and 4-O-acetyl-1-deoxy-1-(pyridyl-2-thio)-α- and -δ-L-cladinoside (Example 1(d)) (953.5 mg) were dissolved in dry acetonitrile (20 mL) under dry argon. A solution of anhydrous silver perchlorate (750.5 mg) in dry acetonitrile (20.6 mL) was added and the mixture was stirred under dry arcon at 25° C. for 23 h. The mixture was evaporated to dryness and the residue was taken up in dichloromethane and washed with water, the pH being adjusted to 10. The organic layer was dried (MgSO₄), filtered and evaporated to dryness. The residue was chromatographed on a silica gel column (60×2 cm) using 25% acetone in hexane (v/v) as the eluant. The product was rechromatographed on a silica gel column (60×2 cm) using 15% acetone in chloroform (v/v) as the eluant to give 2'',4'',4''''-tri-acetyl-O-(4'-O-acetyl-α-L-cladinosyl)-(1→3)-desmycosin (167 mg., 41%) as a colorless amorphous solid (Anal.: found: C, 60.11; H, 8.11; N, 1.26%; C₅₅H₈₇NO₂₁ requires: C, 60.15; H, 7.98; N, 1.28%); MS: m/z 1098 (MH⁺); Rotation: $[α]_D^{26}$ −35.1° (CHCl₃); UV: λ$_{max}$ (CF₃CH₂OH) 285 nm (ε22,465); IR: ν$_{max}$ 1740, 1680, 1595, 1240, 1168, 1050 cm⁻¹; ¹HMR: δ$_H$ (CDCl₃) 0.90 (3H,t,J₁₆,₁₇-CH₃ 7 Hz, 17-CH₃), 0.91 (3H,d,J 7 Hz, CH₃), 1.07 (3H,s,3'-CH₃), 1.08 (3H,d,J 7 Hz, CH₃), 1.13 (3H,d,J 7 Hz, CH₃), 1.16 (3H,d,J 7 Hz, CH₃), 1.20 (3H,d,J 7 Hz, CH₃), 1.79 (3H,d,J₁₂-CH₃,13 1 Hz, 12-CH₃), 2.04 (3H,s,4''-OCOCH₃), 2.05 (3H,s,2''-OCOCH₃), 2.12 (6H,s,4'-OCOCH₃ and 4''''-OCOCH₃), 2.37 (6H,s,3''-N(CH₃)₂), 3.19 (3H,s,3'-OCH₃), 3.47 (3H,s,2'''-OCH₃), 3.53 (3H,s,3''''-OCH₃), 4.46 (1H,d,J₁''ax,2''ax 8 Hz, H₁''ax), 4.62 (1H,d,J₁'''ax,2''''ax 8 Hz, H₁'''ax), 5.00 (1H,dd,J₁'eq,2'eq 1 Hz, J₁'eq,2'ax 4 Hz, H₁'eq), 5.88 (1H,dq,J₁₂-CH₃,13 1 Hz, J₁₃,₁₄ 10 Hz, H₁₃), 6.25 (1H,d,J₁₀,₁₁ 16 Hz, H₁₀), 7.31 (1H,d,J₁₀,₁₁ 16 Hz, H₁₁), and 9.70 (1H,s,H₂₀).

EXAMPLE 5

2'',4'',4''''-Tri-α-Acetyl-O-(4'-α-phenoxyacetyl-α-L-cladinosyl)-(1→3)-desycosin (a) 1,4-Di-O-phenoxyacetyl-δ-L-cladinose (i) L—Cladinose (Example 1(a)) (2.85 c) and oyridine (19.65 mL) were dissolved in dry dichloromethane (84 mL) and the solution was cooled to 0° C. under argon. A solution of phenoxyacetyl chloride (11.2 mL) in dry dichloromethane (84 mL) was added dropwise to the stirred solution over 1 h. The mixture was stirred at 0° C. for 2.5 h. The mixture was diluted with dichloromethane and the washed with water, the pH being adjusted to 10. The organic layer was dried (MgSO₄), filtered and evaporated to dryness. The residue was azeotroped with toluene and chromatographed on a silica gel column (30×5 cm) using 1.5% acetone in chloroform (v/v) as the eluant to give 1,4-di-O-phenoxyacetyl-β-L-cladinose (3.3 g, 46%) as a colourless gum (Anal.: found: C, 61.97; H, 6.20%; C₂₄H₂₈O₈ requires: C, 64.85; H, 6.35%); MS: m/z 293 (MH⁺—OCOCH₂OC₆H₅); Rotation: $[α]_D^{26}$ −26.0° (CHCl₃); UV: λ$_{max}$ (CH₃OH) 206 nm (ε13,285), 260 nm (ε1,418), 266 nm (ε2,012), 273 nm (ε1,601); IR: ν$_{max}$ (CDCl₃) 1775, 1598, 1590, 1490, 1273, 1075, 1030 cm⁻¹; ¹H-MR: δ$_H$(CDCl₃) 1.17 (3H,s,3-CH₃), 1.18 (3H,d,J₅ax,6-CH₃ 7 Hz, 6-CH₃), 1.63 (1H,dd,J₁ax,2ax 10 Hz, J₂eq,2ax 15 Hz, H₂ax), 2.34 (1H,dd,J₁ax,2eq 4 Hz, J₂eg,2ax 15 Hz, H₂eq), 3.31 (3H,s,3-OCH₃), 4.20 (1H,dq,J₄ax,5ax 10 Hz, J₅ax,6-CH₃ 7 Hz, H₅ax), 4.66 (1H,d,J 16 Hz, 1-OCOCH₂OC₆H₅), 4.71 (1H,d,J 16 Hz, 1-OCOCH₂OC₆H₅), 4.73 (1H,d,J 16 Hz, 4-OCOCH₂OC₆H₅), 4.78 (1H,d,J 16 Hz, 4-OCOCH₂OC₆H₅), 4.82 (1H,d,J₄ax,5ax 10 Hz, H₄ax), 6.08 (1H,dd,J₁ax,2eq 4 Hz, J₁ax,2ax 10 Hz, H₁ax), 6.94 (4H,d,J 9 Hz, 1- and 4-OCOCH₂OC₆H₅ (H₂ and H₆)), 7.05 (2H,dd,J 9 Hz, J 9 Hz, 1- and 4-OCOCH₂OC₆H₅ (H₄)) and 7.35 (4H,dd,J 9 Hz, J 9 Hz, 1- and 4-OCOCH₂OC₆H₅ (H₃ and H₅)).

(ii) L—Cladinose(10.82 g) and pyridine (75.2 mL) were dissolved in dry dichloromethane (160 mL). A solution of phenoxyacetic anhydride (87.9 g) in dry dichloromethane (160 mL) was added dropwise to the stirred solution at 25° C. over 30 m. The mixture was diluted with dichloromethane and washed with water, the oH being adjusted to 10. The organic layer was dried (MgSO₄), filtered and evaporated to dryness. The residue was azeotroped with toluene and chromatographed by preparative HPLC on two silica gel cartridges using dichloromethane as the eluant to give 1,4-di-O-phenoxyacetyl-α-L-cladinose (17) (21.75 g., 80%) which was identical with that prepared in 5(a) (i) above.

(b) 4-O-Phenoxyacetyl-α- and -δ-L-cladinose 1,4-Di-O-phenoxyacetyl-δ-L-cladinose (63.35 q) was dissolved in acetonitrile (4.5 L) and 0.1N hydrochloric acid (4.158 L) was added and the mixture was stirred at 25° C. for 18 h. The reaction mixture was neutralized to pH 7.3 and the acetonitrile was evaporated in vacuo. The resulting aqueous solution was extracted with diethyl ether (2xl.5 L) and then with extracts dichloromethane (2xl.5 L). The combined organic were evaporated to dryness and the residue was chromatographed on a preparative HPLC using two silica gel cartridges. The material was eluted using first dichloromethane and then 5% acetone in dichloromethane (v/v) to give 4-O-phenoxyacetyl-α- and 8-L-cladinose (32 g., 72%) as a colorless gum that was used directly in the following experiment.

(c) 1-Deoxy-4-O-ohenoxyacetyl-1-(pyridyl-2-thio-α- and -β-L-cladinoside

4-O-Phenoxyacetyl-α- and -β-L-cladinose (32 g) were dissolved in dry dichloromethane (288 mL) and the solution was cooled to 14° C. A chilled solution of 2,2′dioyridyldisulfide (Available from Aldrich Chemical Co. as Aldrithiol-2) (29.53 g) and tri-n-butylphosphine (36.3 mL) in dry dichloromethane (288 mL) was added in one portion. The mixture was allowed to remain at 14° C. under dry argon for 20 h. The mixture was washed with water, the pH being adjusted to 10. The organic layer was dried ($MgSO_4$), filtered and evaporated to dryness. The residue was chromatographed on a preparative HPLC using two silica gel cartridges. The material was eluted first with hexane (4 L.), then with 25% dichloromethane in hexane (4 L.), dichloromethane (4 L.) and finally 2% acetone in dichlormethane (4 L.) (v/v), to give a mixture of 1-deoxy-4-O-phenoxyacetyl-1-(pyridyl-2-thio)-α- and -- and -L-cladinoside (36.7 g., 88%) (49% α;

An aliquot was rechromatographed on a silica gel column (20×5 cm) using dichloromethane and then 0.5% acetone in dichlormethane (v/v) as the eluant to give from the more polar fractions, the pure β-anomer as a colorless solid; m.p. 74.5°–79° C., (Anal.: found: C, 62.28; H, 6.26; N, 3.82; S, 7.72%. $C_{21}H_{25}NO_5S$ requires: C, 62.51; H, 6.25; N, 3.47; S, 7.95%); MS: m/z 404 ($MH^+$); Rptation: $[\alpha]_D^{26}$ +13.9° ($CHCl_3$); UV: $\lambda_{max}$ ($CF_3CH_2OH$) 237 nm (ε7,991), 268 nm (ε4,479), 274 nm (ε5,258), 280 nm (ε4,883); IR: $\nu_{max}$ ($CDCl_3$) 1760, 1734, 1596, 1572, 1190, 1065, 1005 $cm^{-1}$; $^1$H-NMR $\delta_H$ ($CDCl_3$) 1.16 (3H,d,$J_{5ax,6-CH_3}$ 7 Hz, 6-$CH_3$), 1.18 (3H,s,3-$CH_3$), 1.86 (1H,dd,$J_{1ax,2ax}$ 12 Hz, $J_{2ec,2ax}$ 15 Hz, $H_{2ax}$), 2.44 (1H,dd,$J_{1ax,2eq}$ 3 Hz, $J_{2eq,2ax}$ 15 Hz, $H_{2eq}$), 3.32 (3H,s,3-$OCH_3$); 4.18 (1H,dq,$J_{5ax,6-CH_3}$7 Hz, $J_{4ax,5ax}$ 10 Hz, $H_{5ax}$), 4.74 (1H,d,J 16 Hz, 4-$OCOCH_2OC_6H_5$), 4.78 (1H,d,J 16 Hz, 4-$OCOCH^2OC_6H_5$), 4.86 (1H,d,$J_{4ax,5ax}$ 10 Hz, $H_{4ax}$), 5.74 (1H,dd,$J_{1ax,2eq}$ 3 Hz, $J_{1ax,2ax}$ 12 Hz, $H^1$ax), 6.94 (2H,d,J 9 Hz, 4-$OCOCH_2OC_6H_5$ ($H_2$ and $H_5$)), 7.03 (1H,dd,J 9 Hz, J 9 Hz, 4-$OCOCH_2OC_6H_5$ ($H_4$), 7.03 (1H,m,1-S-$C_4H_4N(H_5)$), 7.32 (2H,dd,J 9 Hz, J 9 Hz, 4-$OCOCH_2OC_6H_5$ ($C_2$ and $C_5$)), 7.35 (1H,m,1-S—$C_5H_4N(H_3)$), 7.58 (1H,ddd,$J_{3,4}$=$J_{4,5}$=9 Hz, $J_{4,6}$ 2.5 Hz, 1-S-$C_5H$ $_4N(H_4)$) and 8.48 (1H,m,1-S-$C_5H$ $_4N(H_6)$). The less polar fractions were combined and rechromatographed on a silica gel column (15×5 cm) using 2.5% acetone in hexane as the eluant to give the pure α-anomer as a colorless solid, m.p. 131°–133.5° C., (Anal.: found: C, 62.69; H, 6.29; N, 3.32; S, 8.18%. $C_{21}H_{25}NO_5S$ requires: C, 62.51; H, 6.25;N 3.47; S, 7.95%), MS: 272.1° ($CHCl_3$); UV: m/z 404 ($MH^+$); Rotation: $[\alpha]_D^{26}$ −$\lambda_{max}$ ($CF_3CH_2OH$) 237 nm (ε15,737), 268 nm (ε8,675), 274 nm (ε10,067), 281 nm (ε9,180); IR: $\nu_{max}$ ($CDCl_3$) 1760, 1595, 1575, 1190, 1063 $cm^{-1}$; $^1$H-NMR; $\delta_H$($CDCl_3$) 1.13 (3H,d,$J_{5ax,6-CH_3}$ 7 Hz, 6-$CH_3$), 1.18 (3H,s,3-$CH_3$), 2.21 (1H,dd,$J_{1eq,2ax}$ 6 Hz, $J_{2eq,2ax}$ 15 Hz, $H_{2ax}$), 2.50 (1H,dd,$J_{1eq,2eq}$ 1 Hz, $J_{2eq,2ax}$ 15 Hz, $H_{2eq}$), 3.34 (3H,s,3-$OCH_3$), 4.53 (1H,dq,$J_{4ax,}$5ax 10 Hz, $J_{5ax,6-CH_3}$ 7 Hz, $H_{5ax}$), 4.75 (1H,d,J 16 Hz, 4-$OCOCH_2OC_6H_5$, 4.79 (1H,d,J 16 Hz, 4-$OCOCH_2$ $OC_6H_5$), 4.86 (1H,d,$J_{4ax,5ax}$ 10 Hz, $H_{4ax}$), 6.44 (1H,dd,$J_{1eq,2eq}$ 1 Hz, $J_{1eq,}$2ax 6 Hz, $H_{1eq}$), 6.96 (2H,d,J 9 Hz, 4-$OCOCH_2OCO$ $_6H_5$ ($H_2$ and $H_6$)), 7.06 (1H,dd,J 9 Hz J 9 Hz, 4-$OCOCH_2OC_6H_5$ ($H_4$)), 7.06 (1H,m,1-S-$C_5H_4N(H_5)$), 7.34 (2H,dd,J 9 Hz, $J_9$ Hz, 4-$OCOCH_2OC_5H_5$ ($H_3$ and $H_5$)), 7.34 (1H,m,1-S-$C_5H_4$ ″$N(H_3)$), 7.56 (1H,ddd,$J_{3,4}$=$J_{4,5}$=9 Hz, $J_{4,6}$ 2.5 Hz, 1-S-$C_5H$ $_4N(H_4)$) and 8.52 (1H,m,n 1-S-$C_5H$ $_4N(H_6)$). (d) 2″,4″,4‴-Tri-O-acetyl-O-(4′-O-phenoxyacetyl-α-L-cladinosyl)-(1→3)-desmycosin.

2′4′,4″-Tri-O-acetyldesmycosin (Example 4(a)) (2.5 g.) and 1-deoxy-4-O-phenoxyacetyl-1-(pyridyl-2-thio)-α- and -α-L-cladinoside (Example 5(c)) (6.2 g.) were added to a solution of anhydrous silver trifluoromethanesulphonate (4.63 g) in dry acetonitrile (100 mL) and the mixture was stirred under dry argon at 25° C. for 20 h. The mixture was evaporated to dryness and the residue was taken up in dichlormethane and washed with water, the pH being adjusted to 10. The organic layer was dried ($MgSO_4$), filtered and evaporated to dryness. The residue was chromatographed on a silica gel column (15×5 cm) using 11% acetone in hexane (v/v) as the eluant to give two partially purified cuts of the product. Each was rechromatographed on a silica gel column (30×2.5 cm using 20% ethyl acetate in dichloromethane (v/v) to give a combined pure sample of 2″,4″,4‴-tri-O-acetyl-O-(4′0-phenoxyacetyl-α-L-cladinosyl)-(1→3)-desmycosin (1.99 g., 60%) as a colorless amorphous solid (Anal.: found: C, 61.34; H, 7.84; N, 0.88%; $C_{61}H_{91}NO_{22}$ requires: C, 61.55; H, 7.71; N, 1.18%), MS: m/z 1190 ($MH^+$); Rotational: $[\alpha]_D^{26}$ −30.0° ($CHCl_3$); UV: $\lambda_{max}$ ($CF_3CH_2OH$) 284 nm (ε22,451), IR: $\nu_{max}$ ($CDCl_3$) 1740, 1675, 1590, 1230, 1168, 1045 $cm^{-1}$; $^1$H-NMR: $\delta_H$ ($CDCl_3$), 0.89 (3H,t,$J_{16,17-CH_3}$ 7 Hz, 17-$CH_3$), 0.92 (3H,d,J 7 Hz, $CH_3$), 1.05 (3H,s,3′-$CH_3$), 1.10 (3H,d,J 7 Hz, $CH_3$), 1.12 (3H,d,J 7 Hz, $CH_3$), 1.17 (3H,d,J 7 Hz, $CH_3$), 1.21 (3H,d,J 7 Hz, $CH_3$), 1.80 (3H,d,$J_{12}$-$CH_{3,13}$ 1 Hz, 12-$CH_3$), 2.02 (3H,s,4″-$OCOCH_3$), 2.06 (3H,s,2″-$OCOCH_3$), 2.13 (3H,s,4‴-$OCOCH_3$), 2.35 (6H,s,3″-($CH_3)_2$), 3.19 (3H,s,3′-$OCH_3$), 3.46 (3H,s,2‴-$OCH_3$), 3.52 (3H,s,3‴-$OCH_3$), 4.30 (1H,d,$J_{1″ax,2″ax}$ 8 Hz, $H_{1″ax}$), 4.62 (3H,d,$J_{1‴ax,2‴ax}$ 8 Hz, $H_{1‴ax}$), 4.65 (1H,d,J 16 Hz, 4′-$OCOCH_2OC_6H_5$), 4.71 (1H,d,J 16 Hz, 4′-$OCOCH_2OC_6H_5$), 4.89 (1H,m,$H_{15}$), 5.02 (1H,dd,$J_{1′eq,2′eq}$ 1Hz, $J_{1′eq,}$2′ax 4 Hz, $H_1′$eq), 5.86 (1H,dc,$J_{12-CH_3,13}$ 1 Hz, $J_{13,14}$ 10 Hz, $H_{13}$), 6.25 (1H,d,$J_{10,11}$ Hz, $H_{10}$), 6.90 (2H,d,J 9 Hz, 4′-$OCOCH_2OC_6H_5$ ($H_2$ and $H_6$)), 6.98 (1H,dd,J 9 Hz, J 9 Hz 4′-$OCOCH_2OC_6H_5$ ($H_4$)), 7.29 (2H,dd,J 9 Hz, J 9 Hz, 4′-$OCOCH_2OC_6H_5$($H_3$ and $H_5$)), 7.30 (3H,d,$J_{10,11}$ 16 Hz, $H_{11}$), and 9.67 (1H,s,$H_{20}$). The more polar fractions afforded some unreacted 2′,4′,4″-tri-O-acetyldesmycosin (190 mg., μ%).

EXAMPLE 6

O-α-L-Cladinosyl-(1→3)-desmycosin (a) 2',4',4"-Trio-O-acetyldesmycosin (Example 4(a)) (800 mc.) and 4-O-acetyl-1-deoxy-1-(ovridyl-2-thio)-α-and μ-L-cladinoside (Example 1(d)) (1.53 c) were dissolved in dry acetonitrile (32 mL) under dry arcon. A solution of anhydrous silver perchlorate (1.2 g.) in dry acetonitrile (33.1 mL) was added and the mixture was stirred under dry argon at 25° C. for 21 h. The mixture was evaporated to dryness and the residue was taken up in dichlormethane and washed with water, the pH being adjusted to 10. The organic layer was dried (MgSO4), filtered and evaporated to dryness. The residue was chromatographed on a silica gel column (15×5 cm.) using 20% acetone in hexane (v/v) as the eluant to give 2",4",4'"-tri-O-acetyl-O-(4'-O-acetyl-α-L-cladinosyl-(1.3)-desmycosin (602 mg). The latter was dissolved in methanol (14.6 mL) containing 1,8-diazabicyclo[5.4.0]undec-7-ene (0.2768 mL) and the mixture was stirred under dry argon at 25° C. for 44 h. The mixture was evaporated to dryness and the residue was chromatographed on a silica gel column (30×2 cm) using 3% methanol in chloroform (v/v) as the eluant to give cladinosyl-(1.3)-desmycosin (272 mg., 33%) contaminated with about 5–10% of O-α-L-with about 5–10% of O-α-L-cladinsoyl-(1.3)-desmycosin seco acid methyl ester, which cochromatographed with the desired product.

(b) 2",4",4'"-Tri-O-acetyl-O-(4-cladinosyl)-(1.3)-desmycosin (Example 5(d)) (O-phenoxyacetyl-α-L-dissolved in methanol (186 mL) containing triethylamine (3.72 mL) (2% w/v solution) and the mixture was allowed to remain under dry argon at 25° C. for 70 h. The solution was evaporated to dryness and the residue was chromatographed on a silica gel column (60×2.5 cm.) using 4% methanol in chloroform (v/v) as the eluant to give α-L-cladinosyl-(1.3)-desmycosin (1.13 g., 91%) as a O-colorless amorphous solid (Anal.: found: C, 59.15; H, 8.22; N, 1.44. $C_{47}H_{79}NO_{17}$ 0.2 $CHCl_3$ requires: C, 59.17; H, 8.35; N, 1.47%); MS: m/z 930 (MH+); Rotation: $[\alpha]_D^{26}$ −43.8° ($CHCl_3$); UV: $\lambda_{max}$($CH_3OH$) 283 nm (ε20,395); IR: $\nu_{max}$ ($CDCl_3$) 3592, 3550, 1737, 1729, 1674, 1590, 1160, 1057 cm$^{-1}$; $^1$H-NMR: $\delta_H$ ($CDCl_3$) 0.89 (3H,t,$J_{16,17}$-$CH_3$ 7 Hz, 17-$CH_3$), 1.02 (3H,d,J 7 Hz, $CH_3$), 1.16 (3H,s,3'-$CH_3$), 1.20 (3H,d,J 7 Hz, $CH_3$), 1.21 (3H,d,J 7 Hz, $CH_3$), 1.26 (3H,d,J 7 Hz, $CH_3$), 1.27 (3H,d,J 7 Hz, $CH_3$), 1.79 (3H,d,$J_{12}$-CH, 13 1 Hz, 12-$CH_3$), 2.52 (6H,s,3"-N($CH_3$)$_2$), 3.12 3H,s,3'-$OCH_3$), 3.46 (3H,s,2'"-$OCH_3$), 3.60 (3H,s,3'"-$OCH_3$), 4.29 (1H,d,$J_{1'"ax,2"ax}$ 8 Hz, $H_{1'ax}$), 4.54 (1H,d, $J_{1'"ax,2"ax}$ 8 Hz, $H_{1'"ax}$), 4.88 (1H,m,$H_{15}$), 4.92 (1H,dd,$J_{1'eq,2'eq}$ 1 Hz, $J_{1'eq,2'ax}$ 4 Hz, $H_{1'eq}$), 5.87 (1H,dq,$J_{12}$-$CH_{3,13}$ 1 Hz, $J_{13,14}$ 10 Hz, $H_{13}$), 6.23 (1H,d,$J_{10,11}$ 16 Hz, $H_{10}$), 7.32 (1H,d,$J_{10,11}$ 16 Hz, $H_{11}$), and 9.71 (1H,s,$H_{20}$).

EXAMPLE 7

2",4",4'"-Tri-O-acetyl-20-deox20-dihydrα-(4'-(a)-2',4'-Di-O-acphenoxyacetyl-α-L-cladinyl.

20-Deoxα-20-dihydrodesmycosin prepared by reduction of desmycosin tosyl hydrazone with bis(triphenylphosphine) copper (I) tetrahydroborate as described in A.K. Ganguly et al., J. Chem. Soc., Chem. Commun., 1983, 1166 (3q.) and pyridine (3.2 mL were dissolved in dry dichloromethane (430 mL) and acetic anhydride (1.86 mL) was added. The mixture was stirred under dry argon at 25° C. for 42 h. The solution was diluted with dichloromethane and washed with water, the pH being adjusted to 10. The organic layer was dried (McS04), filtered and evaporated to dryness. The residue was chromatographed on a silica gel column (30×2 cm.) using 10% acetone in chloroform (v/v) as the eluant to give 2',4'-di-O-acetyl-20-deoxo -20-dihydrodesmycosin (2.92 g., 88%) as a colorless amorphous solid (Anal.: found: C, 60.77; H, 8.26; N, 1.27%; $C_{43}H_{71}NO_{15}$. 0.1 $CHCl_3$ requires: C, 60.47; H,, 8.38; N, 1.64%); MS: m/z 842 (MH+); Rotation: $[']_D^{26}$ −8.2° ($CHCl_3$); UV: $\lambda_{max}$ ($CF_3CH_2OH$) 283 nm (ε22,537); IR: $\nu_{max}$ ($CDCl_3$) 3560, 1744, 1720, 1678, 1596, 1235, 1168, 1057 cm$^{-1}$; $^1$H-NMR: $\delta_H$ ($CDCl_3$) 0.82 (3H,t,$J_{19,20}$-$CH_3$ 7 Hz, 20-$CH_3$), 0.93 (3H,t,$J_{16,17}$-$CH_3$ 7 Hz, 17-$CH_3$), 0.95 (3H,d,J 7 Hz, $CH_3$), 1.13 (3H,d,J 7 Hz, $CH_3$), 1.18 (3H,d,J 7 Hz, $CH_3$), 1.26 3H,d,J 7 Hz, $CH_3$), 1.78 (3H,d,$J_{12}$-$CH_3,13$ 1 Hz, 12-$CH_3$), 2.05 (3H,s,4'-$OCOCH_3$), 2.06 (3H,s,2'-$OCOCH_3$), 2.34 (6H,s,3'-N($CH_3$)$_2$), 3.48 (3H,s,2"-$OCH_3$), 3.61 (3H,s,3"-$OCH_3$), 4.36 (1H,d,$J_{1'ax,2'ax}$ 8 Hz, $H_{1'ax}$), 4.55 (1H,d,$J_{1'"ax,2"ax}$ 8 Hz, $H_{1"ax}$), 5.86 (1H,dq,$J_{12}$-$CH_{3}'13$ 1 Hz, $J_{13,14}$ 10 Hz, $H_{13}$), 6.28 (1H,d,$J_{10,11}$ 16 Hz, $H_{10}$), and 7.29 (1H,d,$J_{10,11}$ 16 Hz, $H_{11}$).

(b) 2',4'-4"-Tri-O-acetyl-20deoxo-20dihydrodesmycosin

2',4'-Di-O-acetyl-20-deoxo-20-dihydrodesmycosin (2.92 g), 4-N,N-dimethylaminopyridine (87 mg) and triethylamine (5 mL) were dissolved in dry dichloromethane (350 mL) and acetic anhydride (0.336 mL) was added. The mixtuer was stirred under argon at 26° C. for 20 h. The reaction mixture was diluted with dichloromethane and washed with water, the pH being adjusted to 10. The organic layer was dried (MgSo4), filtered and evaporated to dryness. The residue was chromotographed on a silica gel column (30×2 cm.) using 7% acetone in chloroform (v/v) as the eluant to give 2',4',4"-tri-O-acetyl-20-deoxo-20-dihydrodesmycosin (2.42 g., 79%) as a colourless amorphous solid (Anal: found: C, 60.33; H, 8.09; N, 1.57%; $C_{45}H_{73}NO_{16}$. 0.01 $CHCl_3$ requires: C, 60.32; H, 8.21; N, 1.56%); MS: m/z 884 (MH$^+$); Rotation: $[\alpha]_D^{26}$+11.2°) ($CHCl_3$); UV: $\lambda_{max}$ ($CF_3CH_2OH$) 283 nm (ε21,718), IR: $\nu_{max}$($CDCl_3$) 3540, 1742, 1676, 1593, 1238, 1168, 1050 cm$^{-1}$; $^1$H-NMR; $\delta_H$ ($CDCl_3$) 0.83 (3H,t,J $_{19,20-CH_3}$ 7 Hz, 20-$CH_3$), 0.92 (3H,t,$J_{16,17-CH_3}$ 7Hz, 17-$CH_3$), 0.96(3H,d,J 7Hz, $CH_3$), 1.13 (3H,d,J 7 Hz, $CH_3$), 1.17 (3H,d,J 7 Hz, $CH_3$), 1.19 (3H,d,J 7; Hz, $CH_3$), 1.79 (3H,d,$J_{12-CH_3'13}$ 1 Hz, 12-$CH_3$), 2.06 (3H,s,4'-$OCOCH_3$), 2.07 (3H,s,2'-$OCOCH_3$), 2.13 (3H,s,4"-$OCOCH_3$), 2.36 (6H,s,3'-N($CH_3$)$_2$), 3.49 (3H,s,2"-$OCH_3$),3.54(3H,s,3" -$OCH_3$),4.38(1H,d,$J_{1'ax,2'ax}$ 8Hz,$H_{1'ax}$),4.63(1H,d,$J_{1"ax2"ax}$ 8Hz, Hax),5.88(1H,dq,$J_{12-CH_{313}}$ 1 Hz, $J_{13,14}$ 10 Hz, $H_{13}$), 6.29 (1H,d,$J_{10,11}$ 16 Hz, $H_{10}$), and 7.32 (1H,d,$J_{10,11}$ 16 Hz, $H_{11}$)

(c)

2",4",4'"-Tri-α-acetyl-(4'-α.-acetyl-α-L-cladinosyl)-(1.3)-20-deoxo -20-dihαdrodesmycosin 2',4',4"-Tri-O-acetyl-20-deoxo -20dihydrodesmycosin (800 mg) and 4-0-acetyl-1-deoxy-1-(pyridyl-2-thio)-α- and -8-L-cladinoside (Example 1(d) (1.55 g.) were dissolved in dry acetonitrile (34 mL) under dry argon. A solution of anhydrous silver perchlorate (1.22 g.) in dry acetonitrile (34 mL) was added and the mixture was stirred under dry argon at 25° C. for 19 h. The mixture was evaporated to dryness and the residue was taken up in dichloromethane and washed with water, the pH being adjusted to 10. The organic layer was dried (MgSO4), filtered and evaporated to dryness. The residue was chromatographed on a silica gel column (60×2 cm.) using 15% acetone in hexane (u/v) as the eluant to give 2",4",4'''-tri-O-acetyl-(4'-0-acetyl-α-L-cladinosyl)-(1.3)-20-deoxo -20-dihydrodesmycosin (396 mg., 40%) as a colorless amorphous solid; MS: m/z 1082 (MH+).

(d) 2",4",4'''-Tri-O-acetyl20-deoxo -20-dihydro-O-(4'0-phenoxyacetyl-α-L-cladinosyl)-(1.3)-20-deoxo -desmycosin 2',4',4"-Tri-O-acetyl-20-deoxo -20dihydrodesmycosin (1.83 g.) and 1-deoxy-4-0phe io)-α- and -8-L-cladinoside (4.59 g.) were dissolved in dry acetonitrile (15 mL) under dry argon. A solution of anhydrous silver trifluoromethanesulphonate (3.46 g) in dry acetonitrile (60.1 mL) was added and the mixture was stirred under dry argon at 25° C. for 21 h. The mixture was evaporated to dryness and the residue was extracted with ethyl acetate and filtered. The ethyl acetate extract was evaporated to dryness and the residue was taken up in dichloromethane and washed with water the pH being adjusted to 10. The organic layer was dried (MgSO4), filtered and evaporated to dryness. The residue was chromatographed on a silica gel column (60×2.5 cm.) using increasing to 20% ethyl acetate in dichloromethane (v/v) as the eluant. Overlap fractions were rechromatographed on a silica gel column (30×2.5 cm.) using 15% ethyl acetate in dichloromethane (v/v) as the eluant to give 2",4",4'''-tri-O-acetyl-20-deoxo -20-dihydro-O-(4'-O-phenoxyacetyl-α-L-cladinosyl)-(1.3)desmycosin (1.26 g., 52%) as a colourless amorphous solid (Anal.: found: C, 62.43; H, 7.89; N, 1.24%; $C_{61}H_{93}NO_{21}$ requires: C, 62.28; H, 7.97; N, 1.19%); MS: m/z 1176 ($MH^{30}$); Rotation:$[\alpha_D^{26}$ −33.6° (CHCl3); UV: $\lambda_{max}$ (CF3CH2OH) 210 nm (ε10,676), 282 nm (ε23,146); IR: $\nu_{max}$ (CDCl3) 1740, 1673, 1591, 1235, 1164, 1050, 1016 cm$^{-1}$; 1H-NMR: δH (CDCl3) 0.87 (3H,t,$J_{19,20}$-CH3 7 Hz, 20-CH3), 0.89 (3H,t,$J_{16,17}$-CH3 7 Hz, 17-CH3), 0.94 (3H,d,J 7 Hz, CH3), 1.05 (3H,s,3'-CH3), 1.12 (6H,d,J 7 Hz, CH3), 1.16 (3H,d,J 7 Hz, CH3), 1.17 (3H,d,J 7 Hz, CH3), 1.78 (3H,d,$J_{12}$-CH$_{3,13}$ 1 Hz, 12-CH3), 2.00 (3H,s,4"-OCOCH3), 2.04 (3H,s,2"-OCOCH3), 2.10 (3H,s,4'''-OCOCH3), 2.34 (6H,s,3"(CH3)2), 3.18 (3H,s,3'-OC3), 3.44 (3H,s,2'''-OCH3), 3.50 (3H,s,3'''-OCH3), 4.42 (1H,dd,$J_4'''ax,5"ax$ 10 Hz, $J_3'''ax,4"ax$ 2.5 Hz, $H_4'''ax$), 4.46 (1H,d,$J_{1"ax,2"ax}$ 8 Hz, $H_{1"ax}$), 4.60 (1H,d,$J_{1'''ax,2'''ax}$ 8 Hz, $H_{1'''ax}$), 4.64 (1H,d,J 16 Hz, 4'-OCOCH2OC6H5), 4.70 (1H,d,J 16 Hz, 4'-OCOCH2OC6H5), 4.73 (H,dd,$J_{3"ax,4"ax}=J_{4"ax,5"ax}$=10 Hz, $H_4"ax$), 4.76 (1H,d,$J_{4'ax,5'ax}$ 10 Hz, $H_4'ax$), 4.84 (1H,dd,$J_{1'eq,2'eq}$ 1 Hz, $J_{1'eq,2'ax}$ 4 Hz, $H_{1'eq}$), 4.86 (1H,m,$H_{15}$), 4.88 (1H,dd,$J_{1"ax,2"ax}$ 8 Hz, $J_{2"ax,3"ax}$ 10 Hz, $H_{2"ax}$), 5.81 (1H,dq,$J_{12}$-CH$_{3'13}$ 1 Hz, $J_{13,14}$ 10 Hz, $H_{13}$), 6.22 (1H,d,$J_{10,11}$ 16 Hz, $H_{10}$), 6.89 (2H,d,J 9 Hz, 4'-OCOCH2OC6H5 (H2 and H6)), 6.97 (1H,dd,J 9 Hz, J 9 Hz, 4'-OCOCH2OC6H5 (H4)), 7.24 (2H,dd,J 9 Hz, J 9 Hz, 4'-OCOCH2OC6H5 (H3 and H5)), and 7.27 (1H,d,$J_{10,11}$ 16 Hz, $H_{11}$) The more polar fractions afforded unreacted 2',4',4"-tri-O-acetyl-20-deoxo -20-dihydrodesmycosin (490 mc., 27%).

EXAMPLE 8

O-α-L-Cladinosyl-(1 3)-20-deoxo -20-dihdyrodesmycosin (i) 2",4",4'''-Tri-O-acetyl-(4'-O-acetyl-α-L-cladinosyl)-(1.3)-20-deoxo -20-dihydrodesmycosin (Example 7(c)) (456 mg.) was dissolved in methanol (11.1 mL) containing 1,8-diazabicyclo[5.4.0]undec-7-ene(0.21 mL) (1.93% w/v solution) and the mixture was stirred under argon at 25° C. for 45 h. The mixture was evaporated to dryness and the residue was chromatographed first on a silica gel column (30×2 cm.) using 3.3% methanol in chloroform (v/v) as the eluent, and then on a silica gel column (30×2 cm.) using 4% methanol in chloroform (v/v) 3)-20-deoxo-20as the eluant to give O-α-L-cladinosyl-(1 dihydrodesmycosin (241 mc) which contained about 33% of O-α-L-cladinosyl-(1.3)-20-deoxo -20-dihydrodesmycosin seco acid methyl ester; MS: m/z 948 (MH+) which could not be separated in anv of the chromatoqraphic systems tried. Additional signals arising from the seco acid methyl ester were also evident in the 1H-NMR: δH (CDCl3) 1.88 (3H,s,$J_{12}$-CH$_{3'13}$ 1 Hz, 12-CH3), 3.23 (3H,s,3'-OCH3), 3.55 (3H,s,1-COOCH3), 4.26 (1H,d,$J_{1"ax,2"ax}$ 8 Hz, $H_{1"ax}$), 4.57 (1H,d,$J_{1'''ax,2'''ax}$ 8 Hz, $H_{1'''ax}$), 5.97 (1H,dq, $J_{12}$-CH$_{3'13}$ 1 Hz, $J_{13,14}$ 10 Hz, $H_{13}$), 6.23 (1H,d,$J_{10,11}$ 16 Hz, $H_{10}$), and 7.64 (1H,d,$J_{10,11}$ 16 Hz, $H_{11}$).

(ii) 2",4",4'''-Tri-O-acetyl-20-deoxo -20-dihydro -O-(4'-O-phenoxyacetyl-α-L-cladinosyl)-(1→3)-desmycosin (Example 7(d)) (683 mg) was dissolved in methanol (81.7 mL) containing triethylamine (1.633 mL)(2% w/v solution) and the mixture was stirred at 25° C. for 94 h. The solution was evaporated to dryness and the residue was chromatographed on a silica gel column (30×2.5 cm) using methanol in chloroform (v/v) as the eluant to give O-α-L-cladinosyl-(1→3)-20-deoxo -20-dihydrodesmycosin (458 mg., 86%) as a colorless amorphous solid (Found: C, 1.11; H, 8.66; N, 1.43%; $C_{47}H_{81}NO_{16}$ requires C, 61.62; H, 8.91; N, 1.53%); MS: m/z 916 (MH+); Rotation: $[\alpha]_D^{26}$ −45.0° (CHCl3); UV: λmax (CH3OH) 282 nm (ε19,398), IR: $\nu_{max}$ (CDCl3) 3590, 3533, 1736, 1673, 1591, 1160, 1074, 1058 cm$^{-1}$; 1H-NMR: δ$_H$ (CDCl3) 0.89 (3H, t, $J_{19,20}$-CH3 7 Hz, 20-CH3), 0.91 (3H,t,$J_{16,17}$-CH3 17-CH3), 1.02 3H,d,J 7 Hz, CH3), 1.17 (3H,s,3'-CH3), 1.19 (3H,d,J 7 Hz, CH3), 1.25 (3H,d,J 7 Hz, CH3), 1.26 (3H,d,J 7 Hz, CH3), 1 27 (3H,d,J 7 Hz, CH3), 1.79 (3H,d,$J_{12}$-CH$_{3,13}$ 1 Hz, 12-CH3), 2.55 (6H,s,3'''-N(CH3)2), 3.16 (3H,s,3'-OCH3), 3.46 (3H,s,2'''-OCH3), 3.60 (3H,s,3'''-OCH3), 4.32 (1H,d,$J_{1"ax,2"ax}$ 8 Hz, $H_{1"ax}$), 4.54 (1H,d,$J_{1'''ax,2'''ax}$ 8 Hz, $H_{1'''ax}$), 4.77 (1 Hz, $J_{1'eq,2'ax}$ 4 Hz, $H_{1'eq}$), 4.88 (1H,dd,$J_{1'eq,2'eq}$ (1H,m,$H_{15}$), 5.84 (1H,dq,$J_{12}$-CH$_{3'13}$ 1 Hz, $J_{13,14}$ 10 Hz, $H_{10}$), and 7.27 (1H,d,$J_{10,11}$ $H_{13}$), 6.21 (1H,d,$J_{10,11}$ 16 Hz, 16 Hz, $H_{11}$).

EXAMPLE 9

O-α-'-L-Cladinosyl-(1.3)-19-deformyldesmycosin (a) 19-Deformyldesmycosin

Desmycosin (Merck Index, Tenth Edition o. 1405) (18.9 o) was dissolved in degassed benzene (580 mL) and tris(triphenYlphospbine)rhodium chloride (29.5 o.) was added. The mixture was heated under drY nitroqen at 90° C. for 16 h. The mixture was diluted with ethyl acetate and extracted twice with 0.2N hydrochloric acid. The agueous acid layer was adjusted to pH 10 and extracted with dichloromethane. The latter was dried (MgSO$_4$), filtered and evaporated to dryness. The residue was chromatographed on a silica gel column (60×5 cm.) using 5% methanol in chloroform (v/v) as the eluant to give 19deformyldesmycosin (13.2 g., 73%) as a colorless amorphous solid (Anal.: found: C, 57.05; H, 7.99; N, 1.62%. C$_{38}$H$_{65}$NO$_{13}$. 0.5 CHCl$_3$ requires C, 56.79; H, 8.15; N, 1.74%); MS: m/z 744 (MH$^+$); Rotation: [α]$_D^{26}$ 0° (CHCl$_3$); UV: λ$_{max}$ (CH$_3$OH) 282 nm (ε20,676); IR: ν$_{max}$ (CDCl$_3$) 3540, 3450, 1705, 1670, 1590, 1185, 1163, 1055 cm$^{-1}$; $^1$H-NMR: δ$_H$ (CDCl$_3$) 0.92 (3H,t,J$_{16,17-CH3}$ 7 Hz, 17-CH$_3$), 1.02 (3H,d,J 7 Hz, CH$_3$), 1.03 (3H,d,J 7 Hz, CH$_3$), 1.18 (3H,d,J 7 Hz, CH$_3$), 1.26 (3H,d,J 7 Hz, CH$_3$), 1.30 (3H,d,J 7 Hz, CH$_3$), 1.78 (3H,d,J$_{12\text{-}CH3,13}$ 1 Hz, 12-CH$_3$), 2.53 (5H,s,3'-N(CH$_3$)$_2$), 3.48 (3H,s,2''-OCH$_3$), 3.60 (3H,s,3''-OCH$_3$), 4.28 (1H,d,J$_{1'ax,2'ax}$ 8 Hz, H$_{1'ax}$), 4.55 (1H,d,J$_{1''ax,2''ax}$ 8 Hz, H$_{1''ax}$), 4.97 (1H,m,H$_{15}$), 5.82 (1H,dc,J$_{12\text{-}CH3,13}$ 1 Hz, J$_{13,14}$ 10 Hz, H$_{13}$), 6.24 (1H,d,J$_{10,11}$ 16 Hz, H$_{10}$), and 7.24 (1H,d,J$_{10,11}$ 16 Hz, H$_{11}$)

(b) 2',4'-Di-O-acetyl-19-deformyldesmycosin

19-Deformyldesmycosin (12 g) was dissolved in dry acetone (100 mL) and acetic anhydride (7.6 mL) was added. The mixture was allowed to remain at 25° C. for 17 h. The solution was evaporated to dryness and the residue was azeotroped with toluene to give 2',4'-di-O-acetyl-19-deformyldesmycosin (11.5 g., 86%) as a colorless amorphous solid that was used without further purification.

An aliquot (800 mg) was chromatographed on a silica gel column (15×2.5 cm.) using 10% acetone in hexane as the eluant to give 2',4'-di-O-acetyl-19-deformyldesmycosin (680 mg) (Anal.: found: C, 60.86, H, 8.49; N, 1.87%. C$_{42}$H$_{69}$NO$_{15}$ requires: C, 60.92; H, 8.40; N, 1.69%); MS: m/z 828 (MH$^+$); Rotation: [α]$_D$≈+11.9° (CHCl$_3$); UV: λ$_{max}$ (CF$_3$CH$_2$OH) 283 nm (ε23,838); IR: V$_{max}$ 1055 cm$^{-1}$; $^1$H-NMR: δ$_H$ (CDCl$_3$) 0.92 (3H,t,J$_{16,17}$-CH$_3$ 7 Hz, 17-CH$_3$), 0.93 (3H,d,J 7 Hz, CH$_3$), 1.03 (3H,d,J 7 Hz, CH$_3$), 1.14 (3H,d,J 7 Hz, CH$_3$), 1.18 (3H,d,J 7 Hz, CH$_3$), 1.25 (3H,d,J 7 Hz, CH$_3$), 1.77 (3H,d,J$_{12\text{-}CH3,13}$ 1 Hz, 12-CH$_3$), 2.05 (6H,s,2' and 4'-OCOCH$_3$), 2.34 (6H,s,3'-N(CH$_3$)$_2$), 3.46 (3H,s,2''-OCH$_3$), 3.60 (3H,s,3''-OCH$_3$), 4.33 (1H,d,J$_{1'ax,2'ax}$ 8 Hz, H$_{1'ax}$), 4.54 (1H,d,J$_{1''ax,2''ax}$ 8 Hz, H$_{1''ax}$), 4.74 (1H,dd,J$_{3'ax,4'ax}$=J$_{4'ax,5'ax}$=10 Hz, H$_{4'ax}$), 4.90 (1H,dd,J$_{1'ax,2'ax}$ 8 Hz, J$_{2'ax,3'ax}$ 10 Hz, H$_{2'ax}$), 4.92 (1H,m,H$_{15}$), 5.83 (1H,d,J$_{10,11}$ 16 Hz, H$_{10}$), and 7.27 (1H,d,J$_{10,11}$ 16 Hz, H$_{11}$)

(c) 2',4',4''-Tri-O-acetyl-19-deformyldesmYcosin

2',4'-Di-O-acetyl-19-deformyldesmycosin (10.3 g.), 4-dimethylaminopyridine (304 mg) and triethylamine (17.3 mL) were dissolved in dry dichloromethane (300 mL) and acetic anhydride (1.174 mL) was added. The mixture was allowed to remain at 25° C. for 22 h. under dry argon. The mixture was extracted with water at pH 8.5 and the dichloromethane layer was dried (MgSO$_4$), filtered and evaporated to dryness. The residue was chromatographed on a silica cel column (60×5 cm.) using 10% increasing to 15% acetone in hexane (v/v) as the eluant to give 2',4',4''-tri-O-acetyl-19deformyldesmvcosin (8.1 g., 75%) as a colorless amorohous solid (Anal.: found: C, 60.88; H, 8.42; N, 1.31%; C$_{44}$H$_{71}$NO$_{16}$ requires: C, 60.74; H, 8.23; N, 1.61%); MS: m/z 870 (MH$^+$); Rotation: [α]αD$^{26}$ +25.3° (CHCl$_3$); UV: α$_{max}$ (CF$_3$CH$_2$OH) 284 nm (ε22,479); IR: ν$_{max}$ (CDCl$_3$) 3520, 1672, 1590, 1234, 1181, 1161, 1050 cm$^{-1}$; $^1$H-NMR: α$_H$ (CDCl$_3$) 0.90 (3H,t,J$_{16,17\text{-}CH3}$ 7 Hz, 17-CH$_3$), 0.94 (3H,d,J 7 Hz, CH$_3$), 1.03 (3H,d,J 7 Hz, CH$_3$), 1.13 (3H,d,J 7 Hz, CH$_3$), 1.16 (3H,d,J 7 Hz, CH$_3$), 1.18 (3H,d,J 7 Hz, CH$_3$), 1.77 (3H,d,J$_{12\text{-}CH3,13}$ 1 Hz, 12-CH$_3$), 2.05 (6H,s,2' and 4''-OCOCH$_3$), 2.10 (3H,s,4''-OCOCH$_3$), 2.33 (6H,s,3'-N(CH$_3$)$_2$), 3.46 (3H,s,2''-OCH$_3$), 3.51 (3H,s,3''-OCH$_3$), 4.33 (1H,d,J$_{1'ax,2'ax}$ 8 Hz, H$_{1'ax}$), 4.42 (1H,dd,J$_3$''eq,4''ax 3 Hz, J$_{4''ax,5''ax}$ 10 Hz, H$_{4''ax}$), 4.60 (1H,d,J$_{1''ax}$,$_{2''ax}$ 8 Hz, H$_{1''ax}$), 4.75 (1H,dd,J$_{3'ax,4'ax}$=J$_{4'ax,5'ax}$=10 Hz, H$_{4'ax}$), 4.88 (1H,dd,J$_{1'ax2'ax}$ 8 Hz, J$_{2'ax,3'ax}$ 10 Hz, H$_{2'ax}$), 4.92 (1H,m,H$_{15}$), 5.82 (1H,do,J$_{12\text{-}CH3,13}$ 1 Hz, J$_{13,14}$ 10 Hz, H$_{13}$), 6.28 (1H,d,J$_{10,11}$ 16 Hz, H$_{10}$) and 7.26 (1H,d,J$_{10,11}$ 16 Hz, H$_{11}$). The more polar fractions afforded unreacted 2',4'-di-O-acetyl-19-deformyldesmycosin (1.35 g., 13%).

(d) 2'',4'',4'''-Tri-O-acetyl-19-deformyl-O-(4'-O-phenoxyacetyl-α-L-cladinosyl)-(1→3)-desmycosin 2',4',4''-Tri-O-acetyl-19-deformyldesmycosin (2.5 g) and 1-deoxy-40-O-phenoxyacetyl-1-(pyridyl-2-thio)-α- and -β-L-cladinoside (6.38 g.) were dissolved in dry acetonitrile (50 mL) under dry argon. A solution of anhydrous silver trifluoromethanesulphonate (4.8 g.) dissolved in dry acetonitrile (50 mL) was added and the mixture was stirred under dry argon at 25° C. for 20 h. The mixture was evaporated to dryness and the residue was extracted with ethyl acetate and filtered. The ethyl acetate was removed in vacuo and the residue was taken up in dichloromethane and washed with water, the pH being adjusted to 10. The orqanic layer was dried (MgSO$_4$), filtered and evaporated to dryness. The residue was chromatograohed on a silica gel column (30×2.5 cm) using 5% increasing to 20% ethvl acetate in dichloromethane (v/v) as the eluant. The product was rechromatoqraphed on a silica gel column (30×2.5 cm.) using 20% ethyl acetate in dichloromethane as the eluant to give 2'',4'',4'''-tri-O-acetyl-19-deformyl-O-(4'-O-phenoxyacetyl-α-L-cladinosyl)-(1→3)-desmycosin (2.04 g., 61%) as a colorless amorphous solid (Anal.: found: C, 62.00; H, 7.84; N, 1.22%; C$_{60}$H$_{91}$NO$_{21}$ requires C, 62.00; H, 7.89; N, 1.21%); MS: m/z 1162 (MH$^+$); Rotation: [α]D$^{26}$ −23.1° (CHCl$_3$); UV: λ$_{max}$ (CF$_3$CH$_2$OH) 210 nm (ε7,561), 283nm (ε17,856); IR: ν$_{max}$ (CDCl$_3$) 1737, 1673, 1590, 1234, 1188, 1160, 1050, 1012 cm$^{-1}$; $^1$H-NMR: δH (CDCl$_3$) 0.90 (3H,t,J$_{16,17}$-CH$_3$ 7 Hz, 17-CH$_3$), 0.92 (3H,d,J 7 Hz, CH$_3$), 1.03 (3H,d,J 7 Hz, CH$_3$), 1.05 (3H,s,3'-CH$_3$), 1.11 (3H,d,J 7 Hz, CH$_3$), 1.14 (3H,d,J 7 Hz, CH$_3$), 1.17 (3H,d,J 7 Hz, CH$_3$), 1.18 (3H,d,J 7 Hz, CH$_3$), 1.76 (3H,d,J$_{12-CH3'13}$ 1 Hz, 12-CH$_3$), 2.02 (3H,s,4''-OCOCH$_3$), 2.04 (3H,s,2''-OCOCH$_3$), 2.12 (3H,s,4'''-OCOCH$_3$), 2.35 (6H,s,3''-N(CH$_3$)$_2$), 3.21 (3H,s,3'-OCH$_3$), 3.44 (3H,s,2'''-OCH$_3$), 3.51 (3H,s,3'''OCH$_3$), 4.37 (1H,d,J$_{1''ax}$ ,2''ax 8 Hz, H$_{1''ax}$), 4.41 (1H,dd,J$_{3'''eq,4'''ax}$ 2 5 Hz, J$_{4'''ax,5'''ax}$ 10 Hz, H$_{4'''ax}$), 4.60 (1H,d,J$_{1'''ax,2'''ax}$ 8 Hz, H$_{1'''ax}$), 4.66 (1H,d,J 16 Hz, 4'-OCOCH$_2$OC$_6$H$_5$), 4.71 (1H,d,J 16 Hz, 4'O-COCH$_2$ OC$_6$H$_5$), 4.75 (1H,dd,J$_{3''ax,4''ax}$=J$_{4''ax,5''ax}$=10 Hz, H$_{4''ax}$), 4.76 (1H,d,J$_{4'ax,5'ax}$ 10 Hz, H$_{4'ax}$), 4.87 (1H,m,H$_{15}$), 4.90 (1H,dd,J$_{1''ax,2}$''ax 8 Hz, J$_{2''ax,3''ax}$ 10 Hz, H$_{3''ax}$), 4.97 (1H,dd,J$_{1'eq}$,2'eq 1 Hz, J$_{1'eq,2'ax}$ 4 Hz, H$_{1'eq}$), 5.80 (1H,dq,J$_{12}$-CH$_{3,13}$ 1 Hz, J$_{13,14}$ 10 Hz, H$_{13}$), 6.24 (1H,d,J$_{10,11}$ 16 Hz, H$_{10}$), 6.90 (2H,d,J 9 Hz, 4'-OCOCH$_2$OC$_6$H$_5$ (H$_2$ and H$_6$)), 6.97 (1H,dd,J 9 Hz, J 9 Hz, 4'-OCOCH$_2$OC$_6$H$_5$ (H$_4$)), 7.27 (2H,dd,J 9 Hz, J 9 Hz 4'OCOCH$_2$OC$_6$H$_5$(H$_3$ and H$_5$)), and 7.28 (1H,d,J$_{10,11}$ 16 Hz, H$_{11}$) The more polar fractions afforded unreacted 2',4',4"-tri-O-acetyl-19-deformyldesmycosin (450 mg., 18%).

(e) O-α-L-Cladinosyl-(1.3)-19-deformyldesmycosin

2",4",4'''-Tri-O-acetyl-19-deformyl-O-(4'-O-phenoxyacetyl-α-L-cladinosyl)-(1.3)-desmycosin (1.9 g) was dissolved in methanol (165 mL) containing triethylamine (4.546 mL) (2% w/v solution) and the mixture was allowed to remain at 25° C. for 72 h. The solution was evaporated to dryness and the residue was taken up in dichloromethane and washed with water, the pH being adjusted to 10. The organic layer was dried (MgSO4), filtered and evaporated to dryness The residue was chromatographed on a silica cel column (60×2.5 cm.) using 4% methanol in chloroform (v/v) as the eluant. The resulting product was rechromatographed on a silica gel column (15×2.5 cm.) usinc ethyl acetate as the eluant to afford O-α-L-cladinosyl-(1.3)-19-deformyldesmycosin (1.28 g., 87%) as a colourless amorphous solid (Anal.: found: C, 61.40; H, 8.99; N, 1.45%; $C_{46}H_{79}NO_{16}$ requires: C, 61.24; H, 8.83; N, 1.55%); MS: m/z 902 (MH+); Rotation: $[\alpha]_D^{26}$ −35.6° (CHCl3); UV: $\lambda_{max}$ (CH3OH) 382 nm ($\epsilon$20,942); IR: $\nu_{max}$ (CDCl3) 3600, 3558, 3450, 1738, 1732, 1674, 1592, 1160, 1058, 1010 cm$^{-1}$; 1H-NMR: $\delta_H$ (CDCl3) 0.92 (3H,t,$J_{16,17}$-$CH_3$ 7 Hz, 17-$CH_3$), 1.02 (3H,d,J 7 Hz, $CH_3$), 1.07 (3H,d,J 7 Hz, $CH_3$), 1.17 (3H,s,3'CH 3), 1.19 (3H,d,J 7 Hz, $CH_3$), 1.26 (3H,d,J 7 Hz, $CH_3$), 1.27 (3H,d,J 7 Hz, $CH_3$), 1.29 (3H,d,J 7 Hz, $CH_3$), 1.77 (3H,d,$J_{12}$-$CH_{3,13}$ 1 Hz, 12-$CH_3$), 2.50 (6H,s,3"-N($CH_3$)2), 3.17 (3H,s,3'-$OCH_3$), 3.45 (3H,s,2'''-$OCH_3$), 3.60 (3H,s,3'''-$OCH_3$), 4.24 (1H,d,$J_{1"ax,2"ax}$ 8 Hz, $H_{1"ax}$), 4.53 (1H,d,$J_{1'''ax,2'''ax}$ 8 Hz, $H_{1'''ax}$), 4.86 (1H,m,$H_{15}$), 4.90 (1H,dd,$J_{1'eq,2'eq}$ 1 Hz, $J_{1'eq,2'ax}$ 4 Hz, $H_{1'eq}$), 5.82 (1H,dg,$J_{12}$-$CH_{3,13}$ 1 Hz, $J_{13,14}$ 10 Hz, $H_{13}$), 6.23 (1H,d,$J_{10,11}$ 16 Hz, $H_{10}$), and 7.26 (1H,d,$J_{10,11}$ 16 Hz, $H_{11}$).

EXAMPLE 10

α- and -β-O-Tetrahydropyranyl-(1→3)-rosaramicin (a) (1R/S)-S-(Pyridyl-2-thio)-tetrahydropyran Dihydropyran (dry, redistilled) (48 mL) and 2mercaptopyridine (6.66 g.) were dissolved in dry dichloramethane (70 mL) under dry nitrogen. Biorad AG50W-X8 (200–400-mesh) sulphonic acid cation exchange resin (H+form) (23 g.)(dried by azeotroping with toluene) was added and the mixture was stirred in the dark at 25° C. for 72 h. The resin was filtered off, washed with dichloromethane and the combined filtrates were evaporated to dryness. The residue was chromatographed on silica gel column (280 g.) using initially 50% hexane in dichloromethane, followed by 25% hexane in dichloromethane and finally 1% ethyl acetate in dichloromethane (all v/v) as the eluant to give a 30:70 mixture (w/w) of (1R/S)-N-(pyridyl-2-thione)tetrahydropyran and (1R/S)-S-(pyridvl-2-thio)-tetrahydropyran (8.31 g.) The more polar fractions afforded additional pure (1R/S)-S-(pyridyl-2-thio)tetrahydropyran (2.4 g.) upon rechromatoqraphy as described above. In order to obtain analytically pure samples of each component of the mixture, a portion of the mixture (0.65 g.) was rechromatographed on an alumina column (100 mL capacity) using 4% increasing to 6% and then 8% of ethyl acetate in hexane (all v/v) as the eluant to give in the order of elution (1R/S)-S-(pyridyl-2-thio)-tetrahydropyran (177 mg.) as a yellow oil; MS: m/z 196 (MH+); Rotation: $[\alpha]_D^{26}0°$ (CH3OH); UV: $\lambda_{max}$ (CH30H) 242 nm ($\epsilon$9,055), 285 nm ($\epsilon$4,348); IR: $\nu_{max}$ (CHCl3), 1573, 1555, 1427, 1416, 1185, 1121, 1100, 1076, 038, 1008 cm$^{-1}$; 1H-NMR: δH (CDCl3) 1.60–2.00, 2.12 (5H and 1H, m, H2, H3, H4), 3.71 (1H,ddd,$J_{5ax,5eq}$, 12 Hz $J_{4eq,5ax}$ 4 Hz, $J_{4ax,5ax}$ 10.5 Hz, $H_{5ax}$), 4.14 (1H,ddd,$J_{5ax,5eq}$ 12 Hz, $J_{4eq,5eg}$=$J_{4ax,5eq}$=6 Hz, $H_{5eq}$), 5.99 (1H,dd,$J_{1eq,2eq}$5 Hz, $J_{1eq,2ax}$ 5.5 Hz, $H_{1eq}$), 7.06 (1H,ddd,$J_{4,5}$ 8 Hz, $J_{5,6}$ 5 Hz, $J_{3,5}$ 1.2 Hz, 1-S-C-5H4N(H5)), 7.34 (1H,ddd,$J_{3,4}$ 8 Hz, $J_{3,5}$=$J_{3,6}$=1.2 Hz,1-S-C-5H4N(H3)), 7.54 (1H,ddd,$J_{3,4}$=$J_{4,5}$=8 Hz, $J_{4,6}$2 Hz, 1-S-$C_5H_4N(H_4)$), and 8.51 (1H,ddd,$J_{5,6}$ 5 Hz $J_{3,6}$ 1.2 Hz, $J_{4,6}$ 2 Hz, 1-S-$C_5H_4N(H_6)$), and (1R/S)-N-(pyridyl-2-thione)tetrahydropyran (233 mg.) as a yellow oil; MS: m/z 196 (MH+); Rotation: $[\alpha]D_D26$ −0.6° (CH3OH); UV: $\lambda_{max}$ (CH30H) 283 nm ($\epsilon$11,029), 360 am ($\epsilon$6,290); IR: $\nu_{max}$ (CHCl3) 1614, 1527, 1452, 1419, 1253, 1207, 1180, 1115, 1079, 1042 cm$^{-1}$; 1H-NMR: αH (CDCl3) 1.24, 1.60–2.08, 2.50 (1H, 4H and 1H, m, H2, H3, H4), 3.80 (1H,ddd,$J_{5ax,4eq}$4.5 Hz, $J_{5ax,4ax}$=$J_{5ax,5eq}$=111 Hz, $H_{5ax}$), 4.24 (1H,ddd,$J_{5eq}$,5ax 111 Hz, $J_{5eq,4eq}$=$J_{5eq,4ax}$=2 Hz, $H_{5eq}$), 6.70 (1H,dd,$J_{1ax,2ax}$ 10.5 Hz, $J_{1ax,2eq}$ 2.5 Hz, $H_{1ax}$), 6.73 (1H,ddd,$J_{4,5}$=$J_{5,6}$=7 Hz, $J_{3,5}$ 1 Hz, 1-S-C-hd 5H4NS(H5)), 7.19 (1H,ddd,$J_{3,4}$ 9 Hz, $J_{4,5}$ 7 Hz, $J_{4,6}$ 2 Hz, 1-S-$C_5H_4N(H_4)$), 7.68 (1H,ddd,$J_{3,4}$ 9 Hz, $J_{3,5}$=$J_{3,6}$=1 Hz, 1-S-C-αα$N(H_3)$) and 8.04 (1H,ddd,$J_{5,6}$ 7 Hz, $J_{4,6}$ 2 Hz, $J_{3,6}$ 1 Hz, 1-S-C-α$H_4N(H_6)$))

(b) α- and β-O-Tetrahydropyranyl-(1→3)-rosaramicin

2'-O-Acetylrosaramicin (prepared by acetylation of rosaramicin using acetic anhydride in acetone by the method described in H. Reimamm, et al. J. Chem. Soc., Chem. Comm., 1972, 1270) (2 g.), anhydrous silver trifluoromethanesulphonate (6 g.) and dry triethylamine (2.8 mL) were dissolved in dry acetonitrile (30 mL). (1R/S)-S-(pyridyl-2-thio)-tetrahydropyran (4 mL) was added and the mixture was stirred under dry nitrogen at 25° C. for 24 h. The reaction mixture was evaporated to dryness and the residue was taken up in dichloromethane and washed with 5% agueous sodium bicarbonate. The dichloromethane layer was filtered, washed with water, dried (Na2SO4), filtered and evaporated to dryness. The residue was triturated with ethyl acetate and filtered. The solids were washed with ethyl acetate and the combined filtrates were evaporated to dryness. The residue was chromatographed on a silica gel column (200 g.) using 10%, 20%, 25% and finally 45% acetone in toluene (v/v) as the eluant to give a ca. 8:5 mixture of the less polar and more polar diaatereoisomers of 2'-O-acetyl-Q-tetrahydropyranyl-(1→3)-rosaramicin (1.16 g., 51%). The early fractions that were rich in the less polar diastereoisomer (327 mg) were rechromatographed on a silica gel column (32 g.) using acetone: dichloromethane: toluene: (v/v/v) (20:60:44) as the eluant to give the less polar diastereoisomer (190 mg). The latter was taken up in methanol (1.5 mL) and allowed to remain at 25° C. for 17 h. The mixture was evaporated to dryness to give O-tetrahydropyranyl-(1.3)-rosaramicin as a colourless amorphous solid (Found: C, 64.56; H, 8.78; N, 2.27. $C_{36}H_{59}NO_{10}$ requires: C, 64.94; H, 8.93; N; 2.10%; MS: m/z 666 (MH+); Rotation: $[\alpha_D^{26}$−42.5°(CHCl3); UV: $\lambda_{max}$ (CH30H) 240 nm ($\epsilon$12,271); IR: $\nu_{max}$ (CDCl3) 3440, 1740, 1720, 1687, 1619, 1167, 1118, 1076, 1032, 986 cm$^{-1}$; 1H-NMR: $\epsilon_H$ (CDCl3) 0.89 (3H,t,$J_{16,17}$-$CH_3$ 7 Hz, 17-$CH_3$), 1.11 (3H,d,J 7 Hz, $CH_3$), 1.12 (3H,d,J 7 Hz, $CH_3$), 1.13 (3H,d,J 7 Hz, $CH_3$), 1.19 (3H,d,J 7 Hz, $CH_3$), 1.37 (3H,s,12-$CH_3$), 2.27 (6H,s,3'-N($CH_3$)2), 4.14 (1H,d,$J_{1''ax}$,2"ax 8 Hz, $H_{1"ax}$), 4.73 (1H,m,$H_{15}$), 4.76 (1H,dd,$J_{1''eq,2'eq}$ 2 Hz, $J_{1'eq,2'ax}$ 7 Hz, $H_{1'eq}$), 6.36

(1H,d,$J_{10,11}$ 16 Hz, $H_{10}$), 6.52 (l$\alpha$,d,$J_{10,11}$ 16 Hz, $H_{11}$), and 9.66 (1H,s,$H_{20}$) The latter fractions from the original column that were rich in the more polar diastereoisomer (327 mg) were rechromatographed on a silica gel column (40 g.) using frst 10%, then 14% and finally 20% acetone in dichloromethane:toluene::60:44 (v/v) as the eluant to give the more polar diastereoisomer (40 mg.). The latter was taken up in methanol (0.5 mL) and allowed to remain at 25° C. for 17 The solution was evaporated to dryness to qive O-tetrahydropyranyl-(1→3)-rosaramicin as a colourless amorphous solid; MS: m/z 666 (MH+); Rotation: $[\alpha]_D^{26}$ −35.1° (CHCl$_3$); UV: $\lambda_{max}$ (CH$_3$OH) 239 nm ($\epsilon$11,264); IR: $\nu_{max}$ (CHCl$_3$) 3430, 1738, 1725, 1687, 1619, 1178, 1168, 1117, 1078, 1032, 987 cm$^{-1}$; $^1$H-NMR: $\delta_H$ (CDCl$_3$) 0.90 (3H,t,$J_{16,17}$-CH$_3$ 7 Hz, 17-CH$_3$), 1.12 (3H,d,J 7 Hz, CH$_3$), 1.16 (3H,d,J 7 Hz, CH$_3$), 1.18 (3H,d,J 7 Hz,CH$_3$), 1.20 (3H,d,J 7 Hz, CH$_3$), 1.43 (3H,s,12-CH$_3$), 2.29 (6H,s,3″N(CH$_3$)2), 4.30 (1H,d,$J_{1'ax}$,2'ax 7 5 Hz, $H_{1'ax}$), 4.72 (1H,dd,$J_{1'eq,2'eq}$ 2 Hz, $J_{1'eq,2'}$ax 7.5 Hz, $H_{1'}$eq), 4.84 (1H,m,$H_{15}$), 6.42 (1H,d,$J_{10,11}$ 16 Hz, $H_{10}$), 6.59 (1H,d,$J_{10,11}$ 16 Hz, $H_{11}$), and 9.77 (1H,s,$H_{20}$).

EXAMPLE 11

3,4-Di-O-(para-methoxybenzyl)-1-deoxy-1-(pyridyl-2-thio)-$\alpha$- and $\beta$-L-digitoxoside Follow the procedure of Brimacombe et al., J. Chem. Soc., Perkin I, 1982, 2583, to prepare methyl 3-oxo-3-dehydro -L-dicitoxoside which is treated with NaBH$_4$ in methanol to prepare methyl $\alpha$-L-digitoxoside. React methyl $\alpha$-L-digitoxoside with more than two equivalents of para-methoxybenzyl triflate in the presence of excess 2,4,6-trimethylpyridine to obtain methyl 3,4-di -O-(para-methoxybenzyl)-$\alpha$-L-digitoxoside. Contact methyl 3,4,-di-O-para-methoxybenzyl)HCl $\alpha$-L-digitoxoside with 1N aqueous HCl at 25° C. to produce 3,4-di-O-(para-methoxybenzyl)-$\alpha$and 8-L-digitoxose. React a solution of the 3,4,-di-O-(para-methoxybenzyl)$\alpha$- and 8-L-digitoxose in dichloromethane with a solution 2,2'-dipyridyldisulfide and tri-n-butyl phosphine in dichloromethane to produce the title compound.

EXAMPLE 12

3-O-Acetyl-4-O-methyl-1-deoxy-1-(pyridyl-2-thio)-$\alpha$- and $\beta$-L-digitoxoside Treat methyl 3-oxo-3-dehydro-L-digitoxoside with methyltriflate in 2,4,6-trimethylpyridine to obtain methyl 4-O-para-methoxybenzyl-3-oxo-3-dehydro-L-digitoxoside. React methyl 4-O-para-methoxybenzyl-3-oxo3-dehydro-L-digitoxoside with sodium borohydride in methanol to obtain methyl 4-O-methyl-$\alpha$-L-digitoxoside. Treat methyl 4-O-methyl-$\alpha$-L-digitoxoside with 0.1N aqueous HCl to obtain 4-O-methvl-$\alpha$- and $\beta$-L-digitoxose which is reacted sequentially with acetic anhydride in the presence of pyridine and thereafter with 1N aqueous HCl and therafter with a solution of 2,2'-dipyridyldisulfide and tri-n-hutylphosphine in dichlormethane to oroduce the title compound.

EXAMPLE 13

3-O-Methyl-4-O-para-methoxybenzyl-1-deoxY-1-(pyridyl-2-thio)-$\alpha$- and $\beta$-L-digitoxside Treat methyl 3-oxo-3-dehydro-L-digitoxosidwith para-methoxybenzyl triflate ln the presenoe oF 2,4,6-trimethylpyridine to produce methyl 4-O-para-methoxybenzyl-3-oxo-3-dehydro-L-digitoxoside which is thereafter reduced with sodium borohydride in methanol to give methyl 4-O-para-methoxybenzyl-$\alpha$-L-digitoxoside. Contact methyl 4-O-para-methoxybenzyl-$\alpha$-L-digitoxoside sequentially with silver (II) oxide and methyl iodide in dimethylformamide, then with 1N aqueous HCl and finally with 2,2'-dipyridyldisulfide in the presence of tri-n-butylphosphine to give the title compound

EXAMPLE 14

3,4-Di-O-Methyl-1-deoxy-1-(pyridvl-2-thio)-$\alpha$- and -$\beta$-L-digitoxoside Treat methyl $\alpha$-L-digitoxoside with two equivalents of methyl triflate in the presence of 2,6-di-tert-butylpyridine to give methyl 3,4-di-O-methyl-$\alpha$-Ldiqitoxoside which is thereafter sequentially treated with 1N aqueous HCl and then 2,2'-dipyridyldisulfide in the presence of tri-n-butylphosphine to qive the title compound.

EXAMPLE 15

O-$\alpha$-L-Cladinosyl-(1→3)-23-O-demycinosyl-4‴-O-iso-valeryltylosin

Treat 23,2'-di-O-acetyl-23-O-demycinosyl-441-O-is$\alpha$-valerytylosin (prepared as described in co-pending U.S. patent application Ser. No. 812,148, filed Dec. 23, 1985) with 1-deoxy-4-O-phenoxyacetyl-1-(pyridyl-2-thio)-$\alpha$- and -$\beta$-L-cladinoside (Example 5(c)) in the presence of anhydrous silver trifluoromethanesulohonate to afford 23,2″-di-O-acetyl-23-O-demycinosyl-4″-O-iso-valeryl-O-(4'-O-phenoxyacetyl-$\alpha$-L-cladinosyl)-(1→3)-tylosin. Treatment of the latter with 2% (v/v) triethylamine in methanol affords the title compound.

EXAMPLE 1

23,2″-Di-O-acetyl-O-$\alpha$-L-cladinosyl-(1→3)-23-O-demycinosyl-4″-O-iso-valervltylosin Treat 23,2'-di-O-acetyl-23-O-demycinosyl-4″-O-iso-valeryltylosin (prepared as described in co-pending U.S. patent application Ser. No. 812,148, fileed Dec. 23, 1985, especially the acylation Schemes I and II on pages 20–24) with 1-deoxy-4-O-phenoxyacetyl-1-(pyridyl-2-thio)-$\alpha$-and-$\beta$-L-cladinoside (Example 5(c)) in the presence of anhydrous silver trifluoromethanesulphonate to give 23,2″-di-O-acetyl-23-O-demycinosyl-4″-O-iso-valeryl-O-(4'-O-phenoxyacetyl-$\alpha$-L-cladinosyl)-(1→3)-tylosin. Treatment of the latter with 2% (v/v) triethylamine in methanol, followed by subsequent treatment of product with acetic anhydride in acetone, gives the title compound.

EXAMPLE 17

O-(4'-O-Acetyl-$\alpha$-L-cladinosyl)-(1→3)-23-O-demycinosyovlosin

Treat 23,2',4″-tri-O-phenoxyacetyl-23-O-demycinosyl$\alpha$ylosin (prepared by the methods described in co-pending U S. patent application Ser. No. 812,148, filed Dec. 23, 1985, especially the acylation Schemes I and III on pages 20–24) with 1-deoxy-4-O-acetyl-1-(pyridyl-2-thio)-$\alpha$- and -$\beta$-L-cladinoside (Example 1(d)) in the presence of anhydrous silver trifluoromethanesulphonate and subsequently with 2% (v/v) triethylamino in methanol to give the title compound.

an a similar fashion the corresponding 4'-O-propionvl, 4'-O-butyryl and O-(4'-O-iso-valeryl-$\alpha$-L-cladinosyl)-(1→3)-23-O-demycinosyltylosins may be prepared by substitution of an equivalent quantity of propionic anhydride, butyric anhydride or iso-valeric anhydride for acetic anhydride in the preparation of the cladinos derivative described in Example 1 above.

EXAMPLE 18

3-O-(2-Methoxy-1-butyloxymethyl)-12,13-dehydro -12,13deoxorosaramicin

2-Methoxy-1-butanol (prepared by standard methods known in the art, for example those described by C. Neri in European Patent Appl., published Feb. 8, 1984. See also CA, 1984, Vol. 101, 6616f and CA, 1984, Vol. 100, 209159 m.) is reacted with formaldehyde and 90% HCl to qive 2-methoxy-1-butyloxymethyl chloride. The latter reacts with 2'-O-acetyl-12,13-dehydro -12,13deoxorosaramicin of Example 2(a) in the presence of a tertiary amino base, followed by reaction with a lower alkanol such as methanol, to give the title compound.

EXAMPLE 19

O-(1-Ethoxyethyl)-(1→3)-rosaramicin
(a) 2-5-(1-Ethoxyeth1) Mercaptopyridine

2-Mercaptopyridine (0.666. g) was dissolved in dry dichloromethane (7 ml.) and the solution was cooled to 0° C. Ethyl vinyl ether (5 ml) (which had been distilled over sodium) and BioRad 50W×4 sulphonic acid resin (H+ cycle) (2.3 g) were added and the mixture was allowed to warm gradually to 25° C. overnight. After 17h the resin was filtered off and washed with dry dichloromethane. The combined filtrates were evaporated to dryness and the residue was chromatographed on a silica gel column (50 g) using first hexane, then 50% hexane in dichloromethane (v/v), then 25% hexane in dichloromethane (v/v), then dichloromethane, then 1% ethyl acetate in dichloromethane (v/v) and finally 2% ethoxyethyl)-mercaptopyridine, MS: m/z 184 (MH+); $^1$H-NMR: NMR $\alpha_H$ (CDCl$_3$) 1.21 (3H,t,J 7 Hz, OCH$_2$CH$_3$), 1.55 (3H),d,J 7 Hz,

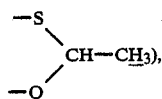

3.50 (2H,m, OCH$_2$CH$_3$), 6.78 (1H,m -1-S-C$_5$H$_4$N), 7.20 (1H,m,1-S-C$_5$H$_4$N), 7.68 (1H,m,1-S-C$_5$H$_4$N) and 7.95 (1H,m, 1-S-C$_5$H$_4$N).

(b) O-(1-Ethoxyethyl)-(1→3)-rosaramcin

2'-O-Acetylrosaramicin (100 mc), 2-S-(1-ethoxyethyl)mercaptopyridine (0.18 ml), anhydrous silver trifluoromethanesulphonate (300 mg) and dry triethylamine (0.14 ml) were dissolved in dry acetonitrile (0.18 ml) and the mixture was stirred at 25° C. for 17h. The solution was evaporated to dryness and the residue was partitioned between 5% aqueous sodium bicarbonataand dichloromethane. The dichloromethane layer was washed with water, dried (Na$_2$SO$_4$), filtered and evaporated to dryness. The residue was chromatographed by preparative thin layer chromatography on 250µ silica gel plates (sisc) using 45% acetone in toluene as the eluant to give 2'-O-acetyl-O-(1-ethoxyethyl)-(1→3)- rosaramicin (18 mg), MS; m/z 696 (MH+) Treatment of the latter with methanol (5 ml) at 25° C. for 17h. afforded O-(1-ethoxyethyl)-(1→3)-rosaramicin.

EXAMPLE 20

O-β-D-Glucopyranonyl-(1→3)-12,13-dehydro-12,13- deoxorosaramicin

Treat 2'-O-acetyl-12,13-dehydro -12,13deoxorosaramicin with 2,3,4,6-tetra-O-acetyl-1-deoxy-1- (pyridyl-2-thio)-α- and -β-D-glucopyranoside (prepared as described in Example 1(d) starting from 2,3,4,6-tetra-O-acetyl-α- and -β-Dglucopyranose, which is prepared as described by J. Fiandor et. al., Synthesis, 1985, pp 1121–1123) in the presence of anhydrous, silver triαluoromethanesulphonate to give the β-D-glycoside, which is then deprotected as described in Example 8 to give the title compound.

What is claimed is:

1. A compound represented by the formula I:

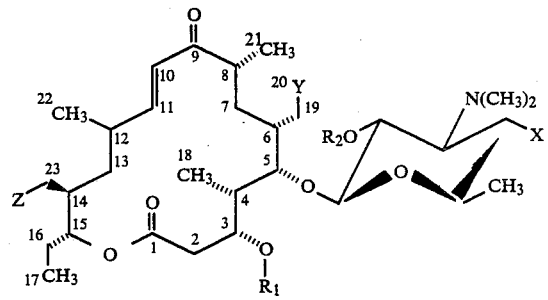

wherein R$_1$ is a glycosyl group represented by the formula II:

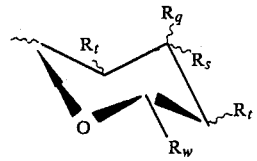

wherein R$_q$ and R$_t$ are independently hydrogen, hydroxy, acyloxy, loweralkoxy, lower alkoxy substituted by phenyl or biphenyl, N-loweralkylaminocarbonyloxy, N-aralkylamino carbonyloxy or arylsulfonyloxy (-OSO$_2$Ar) and R$_s$ and R$_w$ are independently hydrogen, lower alkyl or -CH$_2$OH; with the proviso that at least one of R$_q$, R$_s$, R$_t$ or R$_w$ is not hydrogen; or represented by the formual IIA:

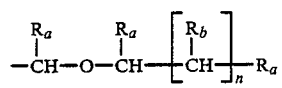

wherein R$_a$ is hydrogen, lower alkyl, or CH$_2$OH and R$_b$ is hydrogen, hydroxy, acyloxy, loweralkoxy, loweralkoxy substituted by phenyl or biphenyl, N-loweralkylaminocarbonyloxy, N-aralkylaminocarbonyloxy or arylsulfonyloxy and n is 1, 2, 3 or 4;

R$_2$ is hydrogen or an acyl group

X is hydrogen, hydroxyl, an acyloxy group

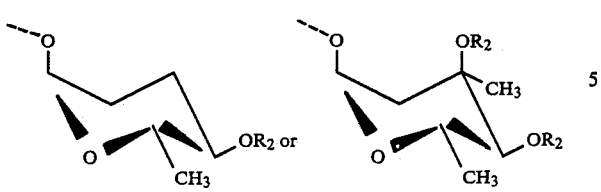

wherein R₂ is defined as hereinabove;

Y is hydrogen, a formyl group, methyl, HC=NNH-aralkyl, wherein aralkyl is lower alkyl substituted by phenyl or biphenyl

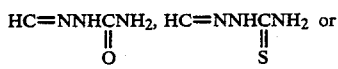

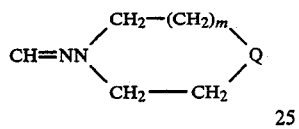

wherein m is 0, 1 or 2 and Q is independently $CR_3R_4$, $NR_3$, O, S, $SO_2$, $CR_3OR_4$,

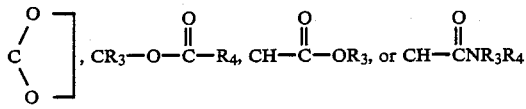

wherein $R_3$ and $R_4$ are independently hydrogen, lower alkyl, lower alkyl substituted by phenyl or biphenyl, G-substituted -(lower alkyl substituted by phenyl or biphenyl), phenyl or biphenyl and G-substituted -(phenyl or biphenyl); wherein G is independently one or more of halogen, trifluoromethyl, lower alkoxy or $(C_2-C_7)$ alkanoyl;

is a 12,13 double bond or a 12,13-oxo moiety;

Z is hydrogen, hydroxy, a acyloxy group, a N,N-di(-loweralkyl) amino group or,

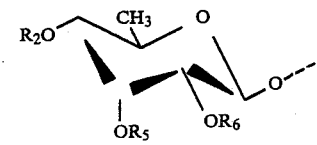

loweralkoxycarbonyloxy, aralkoxycarbonyloxy, N-lowr-alkylaminocarbonyloxy, and N-aralkylaminocarbonyloxy wherein aralkoxy in aralkoxycarbonyloxy is lowralkoxy substituted by phenyl or biphenyl, aralkyl in N-aralkylaminocarbonyloxy is loweralkyl substituted by phenyl or biphenyl, R₂ is defined above and R₅ and R₆ are independently hydrogen, lower alkyl or acyl groups; or a pharmaceutically acceptable acid addition salt thereof.

2. A compound of claim 1 wherein R₁ is an α-L-glycosyl group represented by formula II

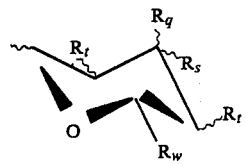

wherein $R_q$ and $R_t$ are independently hydrogen, hydroxy, acyloxy, loweralkoxyl, loweralkoxy substituted by phenyl or biphenyl, N-loweralkylaminocarbonyloxy, N-aralkylaminocarbonyloxy, or arylsulfoxyloxy (-OSO₂Ar) and $R_s$ and $R_w$ are independently hydrogen, lower alkyl or -CH₂OH; with the proviso that at least one of $R_q$, $R_s$, $R_t$ or $R_w$ is not hydrogen.

3. A compound of claim 1 wherein R₁ is α-L-cladinosyl.

4. A compound of claim 1 wherein X is hydrogen.

5. A compound of claim 1 wherein X is hydroxy.

6. A compound of claim 1 wherein X is

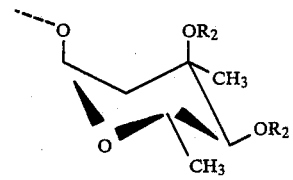

and R₂ is hydrogen or an acyl group.

7. A compound of claim 1 wherein Y is methyl.

8. A compound of claim 1 wherein Y is formyl.

9. A compound of claim 1 wherein  is a 12,13 double bond.

10. A compound of claim 1 wherein  is 12,13-oxo.

11. A compound of claim 1 wherein Z is hydrogen.

12. A compound of claim 1 wherein Z is acyloxy.

13. A compound of claim 1 wherein Z is hydroxy.

14. A compound of claim 1 wherein Z is

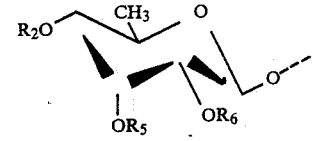

wherein R₂ is hydrogen or an acyl group; and R₅ and R₆ are independently hdyrogen, loweralkyl or an acyl group.

15. A compound of claim 1 wherein X and Z are each hydrogen, Y is formyl or methyl, and  is a 12,13 double hond.

16. A compound of claim 15 wherein R₁ is α-L-cladinosyl and R₂ is hydrogen.

17. A compound of claim 16 wherein Y is methyl which is O-(α-L-cladinosyl)-(1→3)-12,13-dehydro-20-dihydro12,13,20-dideoxorosaramicin.

18. A compound of claim 16 wherein Y is formyl which is O-(α-L- cladinosyl)-(1→3)-12,13-dehydro-12,13-deoxorosaramicin.

19. A compound of claim 15 wherein R₁ is 4-O-acet-yl-α-L-cladinosyl.

20. A compound of claim 19 wherein Y is methyl and R₂ is acetyl which is O-(4'-O-acetyl-α-L-cladinosyl)-(1→3)-2''-O-acetyl-12,13-dehydro-20-dihydro-12,13,20-dideoxorosaramicin.

21. A compound of claim 19 wherein Z is formyl and R₂ is acetyl which is O-(4'-O-acetyl-α-L-cladinosyl)-(1→3)-2"-O-acetyl-12,13-dehydro-12,13-deoxorosaraimicin.

22. A compound of claim 1 wherein R₁ is

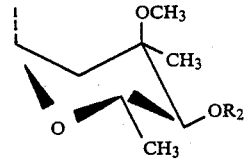

wherein R₁ is a hdyrogen or an acyl group, X is hydroxyl or an acyloxy group ⊄ is a 12,13 double bond and Z is

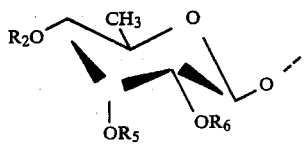

wherein R₂ is a hydrogen or an acyl group and R₅ and R₆ are independently hydrogen, loweralky or an acyl gruop.

23. A compound of claim 22 wherien R₁ is

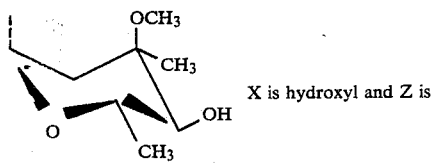

X is hydroxyl and Z is

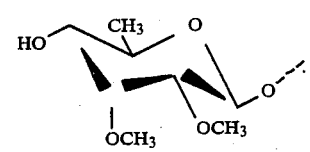

24. A compound of claim 1 wherein R₁ is

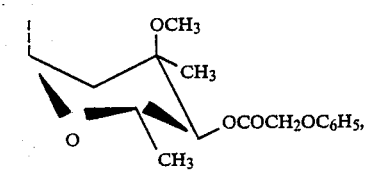

R₂ and X are each acetyl, and Z is

-continued

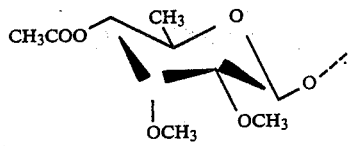

25. A compound of claim 24 where Y is hdyrogen which is 2", 4",4"', tri-O-acetyl-19-deformyl-O-(4'-O-phenoxyacetyl-α-L-cladinosyl)-(1→3)-desmycosin.

26. A compound of claim 24 where Y is formyl which 2",4",4'4-tri-O-acetyl-O-(4'-O-phenoxyacetyl-a-L-cladinosyl)-(1→3)-desmycosin.

27. A compound of claim 24 where Y is methyl which is 2",4",4'41 -tri-O-acetyl -20-deoxo-20-dihydro-O-(4'-O-phenoxyacetyl-α-L-cladinosyl)-(1→3)-desmycosin.

28. A compound of claim 23 where and R₂ are each hydrogen which is O-(α-L-cladinosyl)-(1→3)-19-deformyldesmycosin.

29. A compound of claim 23 wherein Y is methyl and R₂ is hydrogen which is O-(α-L-cladinosyl)-(1→3)-20-deoxo-20-dihydrodesmycosin.

30. A compound of claim 23 wherein Y is formyl and R₂ is hdyrogen which is O-α-L-cladinosyl-(1→3)-desmycosin.

31. A pharmaceutical composition comprising an antibacterially effective amount of a compound of claim 1 in admixtuer with a pharmaceutically acceptable carrier therefor.

32. A pharmaceutical composition of claim 31 wherein in said compound, X and Z are each hydrogen, Y is formyl or methyl, and ⊄ is a 12,13 double bond.

33. A pharmaceutical composition of claim 31 wherein in said compound, R₁ is

R₂ is hdyrogen or an acyl grup, X is hydroxyl or an acyloxy group ⊄ is a 12,13 double bond and Z is

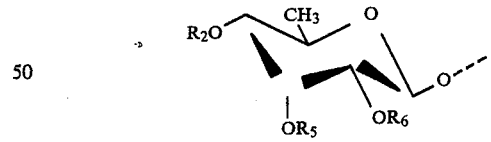

R₂ is hydrogen or an acyl gruop, and R₆ are independently hydrogen lowr alkyl or an acyl gruop.

34. A method of eliciting an antibacterial effect against a susceptible bacterial infection which comprises administering to an animal having a susceptible bacterial infection an antibacterially effective amount of a compound of claim 1 alone or a compound of claim 1 in admixture with a pharmaceutically acceptable carrier therefor.

* * * * *